US010195300B2

(12) United States Patent
Lloyd

(10) Patent No.: US 10,195,300 B2
(45) Date of Patent: Feb. 5, 2019

(54) SYSTEM AND METHOD FOR DISINFECTING AN OCCUPIED AREA USING GERMICIDAL RADIATION BASED ON EYE PROTECTION WORN BY PERSONS IN THE AREA

(71) Applicant: Ralph Birchard Lloyd, Fayetteville, NC (US)

(72) Inventor: Ralph Birchard Lloyd, Fayetteville, NC (US)

(*) Notice: Subject to any disclaimer, the term of this patent is extended or adjusted under 35 U.S.C. 154(b) by 168 days.

(21) Appl. No.: 15/442,289

(22) Filed: Feb. 24, 2017

(65) Prior Publication Data
US 2017/0246331 A1 Aug. 31, 2017

Related U.S. Application Data

(60) Provisional application No. 62/299,827, filed on Feb. 25, 2016, provisional application No. 62/413,012, filed on Oct. 26, 2016, provisional application No. 62/413,029, filed on Oct. 26, 2016.

(51) Int. Cl.
*A61L 2/24* (2006.01)
*A61L 2/08* (2006.01)
*A61L 2/10* (2006.01)

(52) U.S. Cl.
CPC ............ *A61L 2/24* (2013.01); *A61L 2/084* (2013.01); *A61L 2/10* (2013.01); *A61L 2202/14* (2013.01); *A61L 2202/25* (2013.01)

(58) Field of Classification Search
CPC .............. A61L 2/24; A61L 2/084; A61L 2/10
See application file for complete search history.

(56) References Cited

U.S. PATENT DOCUMENTS

| | | | |
|---|---|---|---|
| 5,382,986 A | 1/1995 | Black et al. |
| 5,725,565 A | 3/1998 | Smith |
| 6,171,548 B1 | 1/2001 | Rose et al. |
| 6,656,424 B1 | 12/2003 | Deal |
| 6,911,177 B2 | 6/2005 | Deal |
| 7,175,806 B2 | 2/2007 | Deal et al. |
| 7,415,202 B2 | 8/2008 | Fujimoto et al. |
| 7,692,172 B2 | 4/2010 | Leben |
| 8,097,861 B2 | 1/2012 | Leben |

(Continued)

FOREIGN PATENT DOCUMENTS

| | | |
|---|---|---|
| CN | 205079861 U | 3/2016 |
| WO | 0160419 A1 | 8/2001 |
| WO | 2016061380 A1 | 4/2016 |

OTHER PUBLICATIONS

Reed, N.G., "The History of Ultraviolet Germicidal Irradiation for Air Disinfection", Public Health Reports, Jan. 1, 2010, pp. 15-27, vol. 125, No. 1.

(Continued)

*Primary Examiner* — Regina M Yoo
(74) *Attorney, Agent, or Firm* — Coats & Bennett, PLLC

(57) ABSTRACT

A system and method of disinfecting an area using germicidal radiation. The system is configured to track person within the environment, and to control one or more germicidal radiation emitters based on user and sensor inputs, such as detecting whether the eyes are protected for the persons in this environment. The system is configured to intentionally and safely expose persons in the environment to germicidal radiation. This provides for safe, electronically controlled, direct decontamination of the surfaces, air, and persons in the environment.

20 Claims, 11 Drawing Sheets

(56) References Cited

U.S. PATENT DOCUMENTS

| | | |
|---|---|---|
| 8,127,396 B2 | 3/2012 | Mangiardi |
| 8,294,580 B2 | 10/2012 | Witwer et al. |
| 8,708,141 B1 | 4/2014 | Invie et al. |
| 8,816,301 B2 | 8/2014 | Stibich et al. |
| 8,842,019 B2 | 9/2014 | Boccola |
| 8,877,124 B2 | 11/2014 | Bergman |
| 9,023,274 B2 | 5/2015 | Garner et al. |
| 9,345,798 B2 | 5/2016 | Trapani |
| 9,358,313 B2 | 6/2016 | Deal |
| 2007/0231192 A1 | 10/2007 | Jung et al. |
| 2007/0231194 A1 | 10/2007 | Jung et al. |
| 2009/0263499 A1 | 10/2009 | Platt, Jr. et al. |
| 2011/0288617 A1 | 11/2011 | Sharma |
| 2012/0075464 A1 | 3/2012 | Derenne et al. |
| 2012/0126134 A1 | 5/2012 | Deal et al. |
| 2012/0282135 A1 | 11/2012 | Trapani |
| 2013/0296978 A1 | 11/2013 | Fiset |
| 2015/0258234 A1 | 9/2015 | Larsen |

OTHER PUBLICATIONS

Memarzadeh, F., et al., "Applications of ultraviolet germicidal irradiation disinfection in health care facilities: Effective adjunct, but not stand-alone technology", Association for Professionals in Infection Control and Epidemiology, Inc., American Journal of Infection Control, Jan. 1, 2010, pp. S13-S24, vol. 38, No. 5.

International Search Report dated May 8, 2017 in re International Application No. PCT/US2017/019370 filed Feb. 24, 2017.

"Meet Kinect for Windows." 4 pages. Accessed Feb. 22, 2017 at https://developer.microsoft.com/en-us/windows/kinect. Microsoft.

"Kinect for Windows Programming Guide." 2 pages. Accessed Feb. 22, 2017 at https://msdn.microsoft.com/en-us/library/dn782037(d=printer).aspx. Microsoft.

"Laser Show Projector Specifications." 8 pages. Jan. 13, 2017. Accessed Feb. 22, 2017 at http://lasershowprojector.com/laser-show-projector-specifications/ Projector Refferal Network Inc.

"Laser Show Projectors Explained." 8 pages. Jan. 13, 2017. Accessed Feb. 22, 2017 at http://lasershowprojector.com/laser-show-projectors-explained/ Pangolin Forum.

"Moving head laser projector LPS Impression Laser." 2 pages. Accessed Feb. 22, 2017 at http://www.lps-laser.com/laser-show-with-moving-head-laser-projector-glp-impression-laser.htm. LPS-Lasersysteme, Ofterdingen, Germany.

"LPS Impression Laser." Data Sheet. 1 page. Accessed Feb. 22, 2017 at http://www.lps-laser.com/download/data-sheet-datenblatt/moving-head-laser-projektor-GLP-impression-laser.pdf LPS-Lasersysteme, Ofterdingen, Germany.

"Implementing User Experience Guidelines in Intel® RealSense™ Applications." 9 pages. Jul. 8, 2016. Accessed Feb. 22, 2017 at https://software.intel.com/en-us/articles/implementing-user-experience-guidelines-in-intel-realsense-applications. Intel.

"Smartglasses." 11 pages. Accessed Feb. 22, 2017 at https://en.wikipedia.org/wiki/Smartglasses. Wikipedia, the free encyclopedia.

"Computer vision." 11 pages. Accessed Feb. 23, 2017 at https://en.wikipedia.org/wiki/Computer_vision. Wikipedia, the free encyclopedia.

"OpenCV." 4 pages. Accessed Feb. 23, 2017 at https://en.wikipedia.org/wiki/OpenCV. Wikipedia, the free encyclopedia.

SYSTEM AND METHOD FOR DISINFECTING AN OCCUPIED AREA USING GERMICIDAL RADIATION BASED ON EYE PROTECTION WORN BY PERSONS IN THE AREA

RELATED APPLICATIONS

This application claims the benefit of U.S. Provisional Application No. 62/299,827 filed on Feb. 25, 2016, U.S. Provisional Application Nos. 62/413,012 and 62/413,029, each of which was filed on Oct. 26, 2016. Each of these applications is hereby incorporated by reference in its entirety.

BACKGROUND

Disinfection of areas of medical facilities is a key component to reduce or eliminate hospital acquired infections, also known in the art as nosocomial diseases or infections. The problem has become so serious that many medical facilities close or restrict areas to allow for intensive methods to eradicate the micro-organisms that cause these infections.

Ultraviolet radiation and more recently high intensity narrow spectrum (HINS) light have been found to be ways to treat these areas to reduce the levels of these microorganisms. Ultraviolet germicidal irradiation is a disinfection method that uses ultraviolet radiation at a sufficiently short wavelength to break down these micro-organisms. Ultraviolet-C radiation with a wavelength of between 180-280 nm (and particularly between 240 nm-280 nm) has been found to be particularly effective. UV-B between 280-320 nm also has germicidal properties. The relatively short wavelengths of ultraviolet-C and B radiation are harmful to forms of life at the micro-organic level by destroying the ability of microorganisms to reproduce by causing photochemical changes in nucleic acids in these organisms so that their DNA and/or RNA chemical structure is disrupted. The disruption prevents micro-organisms from replicating, thereby rendering them inactive and unable to cause infection.

Disinfecting using ultraviolet radiation has been limited. This is mainly due to existing systems being configured to require the treated areas to be unoccupied by people. This precaution stems from the fact that UV exposure to unprotected skin can produce various negative effects including erythema, photosensitivity, skin aging, immune system damage, and even increased occurrences of skin cancer. The most serious effects of UV exposure are those which affect the eyes, the results of which can produce photokeratitis and conjunctivitis and other corneal injuries, including potentially cataracts in the eye lens. It so happens that wavelengths most effective for germicidal uses are also the wavelengths that are most destructive to human tissue. Thus, these existing systems cannot be used in areas populated by people who are not properly protected from UV radiation. Or when used, their application is limited to relatively small physical areas such as unoccupied rooms, floors, ductwork, doorways, or ceilings or inside of air purifying devices and the like. Since the 1930's the use of germicidal radiation during surgeries has occasionally been practiced, but in these instances all personnel in the area are fully protected from the UV with clothing, skin creams, and UV eye protection which is administratively controlled for the short duration of the surgery. But overall, germicidal radiation systems are not conducive to treating areas in which people are routinely located, thus limiting the major benefits they can provide. Germicidal radiation, with proper protection, can be superior to other forms of sanitation which are used to reduce microorganism populations, such as periodic cleanings with bleach or emitting a toxic chemical mist into the air. But the inability to ensure administratively that everyone in an area is properly protected at all times and for extended periods of time makes the continuous or semi-continuous use of UV decontamination in the presence of persons infeasible. Being able to track persons in an area exposed to germicidal radiation and monitor whether or not they are properly protected from the germicidal radiation as they go about their routine activities would greatly enable this safe and effective disinfection technology to be much more readily deployed in the fight against pathological microorganisms and will help prevent the development of so called antibiotic-resistant "super-bugs." Continuous electronic monitoring of whether or not persons in the area have adequate skin or eye protection to enable safe exposure to germicidal radiation disinfection is not known in the art.

More recently, other wavelengths of radiation in the visible range have been found to have germicidal activity. High intensity narrow spectrum light (HINS) in the range of 380 to 420 nm, violet light, and particularly the 400-410 nm range centered on 405 nm, has been found to have some germicidal activity. Although these wavelengths are not harmful to humans as is UV radiation, because such high intensities are needed it would not be desirable to expose the unprotected human eyes to HINS, and thus protecting persons within an environment that is being continuously or semi-continuously decontaminated with HINS light is also contemplated in this invention, even though the majority of the discussion centers on the much more studied and practiced decontamination with germicidal radiation. Continuous electronic monitoring of whether or not persons in the area have adequate eye protection to enable safe exposure to HINS light disinfection is not known in the art.

SUMMARY

The present application is directed to the use of sensors and smart technology to manage the safety concerns of germicidal radiation exposure thereby allowing the use of continuous or semi-continuous germicidal radiation to kill or render incapable of reproduction microbes in an environment while patients, healthcare workers, and/or other persons are present. The benefits of this are: (a) microbes in the air, emitted by coughing or sneezing, can be killed before they spread, (b) microbes on surfaces can be killed before being transferred to others, (c) much more active, real time decontamination can be occurring on a continuous basis, rather than relying on periodic chemical cleaning techniques, (d) microbes on the skin and clothing of the patients themselves or other persons can be addressed, thereby helping to prevent the spread of diseases from the patient back to himself or from person to person. Other potential uses of this invention include but are not limited to decontamination of office spaces, governmental complexes, research facilities, portable emergency care facilities, nursing care facilities, homes, schools, food preparation facilities, and even outdoor environments where there is a concern about the spread of infectious diseases. It will be evident to those skilled in the art that this invention has the potential to improve health care outcomes by reducing the number and severity of infections, reducing fatalities from hospital acquired infections, reducing health care costs, and reducing the potential for the development of anti-biotic resistant microorganisms, all of which are urgently needed in the health care system.

The system is configured to track persons within the environment. This can be done by directly detecting and monitoring the presence of persons in the environment or indirectly by assigning each individual adequate Personal Protective Equipment (PPE) and monitoring the location and use of each item of PPE. The system is also configured to control the network of emitters and output of the emitters based on user and sensor inputs, such as detecting whether the eyes and skin are protected for the persons in this network. The system is configured to intentionally and safely expose persons in the environment to germicidal radiation levels that would be considered unsafe if the persons were not protected. This provides for direct decontamination of the air in the environment, the surfaces in the environment, and the skin and clothing of the people in the environment, who are often the sources of the infection or infectious diseases.

One embodiment is directed to a system for disinfecting an environment. The system includes a germicidal radiation emitter that emits germicidal radiation into the environment to disinfect the environment. A sensor is configured to detect whether a person in the environment is wearing eye protection on a head of the person and over eyes of the person. Processing circuitry is communicatively coupled to the germicidal emitter and the sensor. The processing circuitry is configured to operate the germicidal radiation emitter in a first mode in response to detecting that the person is wearing the eye protection, and in a second mode in response to detecting that the person is not wearing the eye protection. The second mode includes a lower amount of germicidal radiation being emitted into the environment than the first mode. The second mode includes either a positive amount of the germicidal radiation being emitted into the environment or no germicidal radiation being emitted into the environment.

The germicidal radiation emitter may emit at least one of UV-C, UV-B, and HINS germicidal radiation into the environment.

The system may include that at least two of the emitter, the sensor, and the processing circuitry transmit data using wireless transmissions.

The system may include a person sensor that senses the environment and transmits signals to the processing circuitry which is configured to determine a number of people in the environment.

The germicidal radiation emitter may be configured to move to different locations within the environment while emitting the germicidal radiation.

The system may include a protection sensor on the eye protection that is configured to sense a position of the eye protection relative to the head of the person and to transmit signals to the processing circuitry. The processing circuitry may be configured to analyze the signals to determine if the eye protection is extending over eyes of the person prior to emitting the germicidal radiation in the first mode.

The system may include a germicidal radiation sensor that is mounted on an inner side of the eye protection to detect an amount of the germicidal radiation that reaches the inner side of the eye protection when the germicidal radiation is emitted and to transmit the amount to the processing circuitry.

The system may include that sensor is a camera to capture images of the environment and the processing circuitry may be configured to analyze the captured images to determine a number of persons in the environment and whether the persons in the environment are wearing the eye protection.

The system may include that the eye protection includes a transparent shield configured to block the germicidal radiation while allowing at least some visible light to pass through.

The eye protection may include one or more transparent sections and a material section that is attached to and extends from the transparent shield and is configured to block the germicidal radiation with the eye protection being sized such that when worn by the person the transparent shield extends over at least one of eyes, head, face, and neck of the person, and the material section extends over the head, face, and neck of the person.

Another embodiment is directed to a system for disinfecting an environment. The system includes a germicidal radiation emitter that emits at least one of UV-B, UV-C, and HINS radiation into the environment at levels to disinfect the environment and in excess of limits considered safe for humans who are not wearing eye protection that extends over eyes of a person. A sensor detects whether the person in the environment is wearing the eye protection. A processing circuit is communicatively coupled to the germicidal radiation emitter and the sensor. The processing circuit is configured to operate the germicidal radiation emitter at levels to disinfect the environment in excess of the limits considered safe for humans who are not wearing the eye protection in response to determining that the person is wearing the eye protection. The processing circuit is configured to operate the germicidal radiation emitter to decrease the germicidal radiation to levels considered safe for humans who are not wearing the eye protection in response to detecting that the person is not wearing the eye protection.

The system may also include a person sensor that senses people in the environment and transmits signals to the processing circuitry which determines a number of people in the environment.

The system may include that the eye protection includes a protection sensor configured to sense a position of the eye protection relative to a body of the person and to transmit signals to the processing circuitry with the processing circuitry configured to analyze the signals to determine if the eye protection is extending over the eyes of the person prior to emitting the germicidal radiation into the environment in excess of limits considered safe for humans who are not wearing the eye protection.

The system may include that the eye protection includes a transparent shield configured to block the germicidal radiation while allowing at least some visible light to pass through with the transparent shield comprising one or more transparent sections and a material section that extends outward and blocks the germicidal radiation. The eye protection is sized such that when worn by the person the transparent shield extends over the eyes of the person and the material section extends over the head, face, and neck of the person.

The system may include a germicidal radiation sensor that is mounted on an inner side of the eye protection to measure an amount of the germicidal radiation that reaches the inner side of the eye protection when the germicidal radiation is emitted with the germicidal radiation sensor configured to transmits the amount to the processing circuitry.

The system may include that the sensor includes a camera to capture images of the environment with the processing circuitry being configured to analyze the captured images to determine a number of persons in the environment and whether each of the persons in the environment is wearing the eye protection.

Another embodiment is directed to a method of disinfecting an environment. The method includes: determining whether a person in the environment is wearing eye protection; in response to determining that the person in the environment is wearing the eye protection, emitting germicidal radiation into the environment at levels to disinfect the environment and in excess of limits considered safe for humans who are not wearing eye protection; and in response to determining that the person in the environment is not wearing the eye protection, emitting a lesser amount of or no germicidal radiation into the environment.

The method may also include a sensor that senses the environment and transmits signals to processing circuitry that determines a number of people in the environment.

The eye protection may include a transparent shield capable of blocking germicidal radiation while allowing at least some visible light to pass through with the transparent shield comprising one or more transparent sections and a material section that is attached to and extends from the transparent shield and is capable of blocking the germicidal radiation. The eye protection is sized such that when worn by the person the transparent shield extends over the eyes of the person and the material section extends over the head, face, and neck of the person.

The method may also include a protection sensor on the eye protection configured to sense a position of the eye protection relative to a body of the person and to transmit signals to processing circuitry with the processing circuitry configured to analyze the signals to determine if the eye protection is extending over eyes of the person prior to emitting the germicidal radiation into the environment in excess of limits considered safe for humans who are not wearing the eye protection.

One embodiment of use includes a method of disinfecting an environment that includes: determining whether there is a person in the environment; in response to determining that there is not a person in the environment, operating the one or more germicidal radiation emitters in a first mode and emitting a first amount of germicidal radiation into the environment; and in response to determining that there is a person in the environment, operating the one or more emitters in a second mode and emitting a second amount of germicidal radiation into the environment, with the second amount of germicidal radiation being different than the first amount of germicidal radiation. Depending on the types of microorganisms being addressed and depending on other user input factors such as power costs, the second amount of radiation can be higher or lower than the first amount. For example, when properly protected persons enter an area, there are more sources and carriers of microorganisms that require decontamination and more potential for air currents and movement to stir up and make airborne bacteria that had settled out on floors and other surfaces. In this scenario it would be desirable to increase the level of germicidal radiation when persons enter the area. In other situations, it may be desirable to more intensely irradiate an area when persons are not present, and decrease the amount of radiation to more tolerable levels when they enter the area with proper protection. In other situations, it may be desirable to irradiate for a brief period of time when no one is present in an area, and then shut off or decrease the radiation to save power, then when properly protected persons enter the area again the germicidal radiation levels can be increased again. Thus, this system can be operated in various ways with and without persons in the area depending on the microorganisms being destroyed and user preferences.

Another embodiment is directed to a method of disinfecting an environment that includes: providing at least one germicidal radiation emitting source located within or near the environment; providing a computerized controller for controlling the output of the germicidal radiation emitter(s) according to a pre-selected mode of operation; providing a means of detecting and determining whether there is a person in the environment; in response to determining that there is not a person in the environment, operating a germicidal radiation emitter in a first mode and emitting germicidal radiation into the environment according to the programmed settings of the first mode; and in response to determining that there is a person in the environment, operating the emitter in a second mode and emitting germicidal radiation into the environment according to the programmed settings of the second mode.

The method may include providing a means to determine whether the eye protection has been properly donned for each person in the environment, and in response to determining that there is at least one person in the environment without properly donned protective eyewear, adjust the source of germicidal radiation to a safe level, with safe levels being defined as those at or below the allowable radiation levels established by the federal or local government or other agency or even the owner of the environment in cases where the owner wishes to establish safe levels that are lower than those established by the government. In some jurisdictions, health care professionals may be granted exemptions from governmental standards and may be allowed to increase levels of radiation above those levels set by the government; in such cases, for the purposes of this invention, safe levels would be defined by the health care professionals in that facility. Safe levels as defined in this application may include levels in which no radiation is being emitted by the emitters.

The method may include providing a means to determine whether skin protection has been properly donned or applied for each person in the environment; and in response to determining that there is a person in the environment without proper skin protection from germicidal radiation, adjust the source of germicidal radiation to a safe level.

The various aspects of the various embodiments may be used alone or in any combination. Also multiple sources of different wavelength germicidal radiation or HINS radiation can be used alone or in any combination, as is desired.

DETAILED DESCRIPTION

The present application is directed to systems and methods for disinfecting an area using germicidal radiation, including ultraviolet and/or HINS light radiation. Although the following description and majority of contemplated applications focuses on UV radiation and emitters, it will be understood that HINS light or other germicidal radiation sources can also be used in a similar manner to the embodiments described herein. The system includes a germicidal radiation emitter configured to emit germicidal radiation into an area, and one or more sensors to detect the existence of a person in the area. The system may further be equipped with a computing device to determine whether the person is equipped with protective equipment, such as eye protection. Based on the information, the system is configured to emit germicidal radiation into the area both where the person is located, as well as other sections of the area.

The systems and methods monitor one or more persons that are in an area of the one or more germicidal emitters. This area is treated with germicidal radiation, including when the one or more persons are present. The treatment includes emitting germicidal radiation onto the one or more persons that are present. The systems and methods monitor the one or more persons to control the extent of germicidal radiation to which the one or more persons are exposed. The monitoring ensures that the one or more persons are exposed to safe levels of germicidal radiation depending upon one or more factors.

Figure 1:
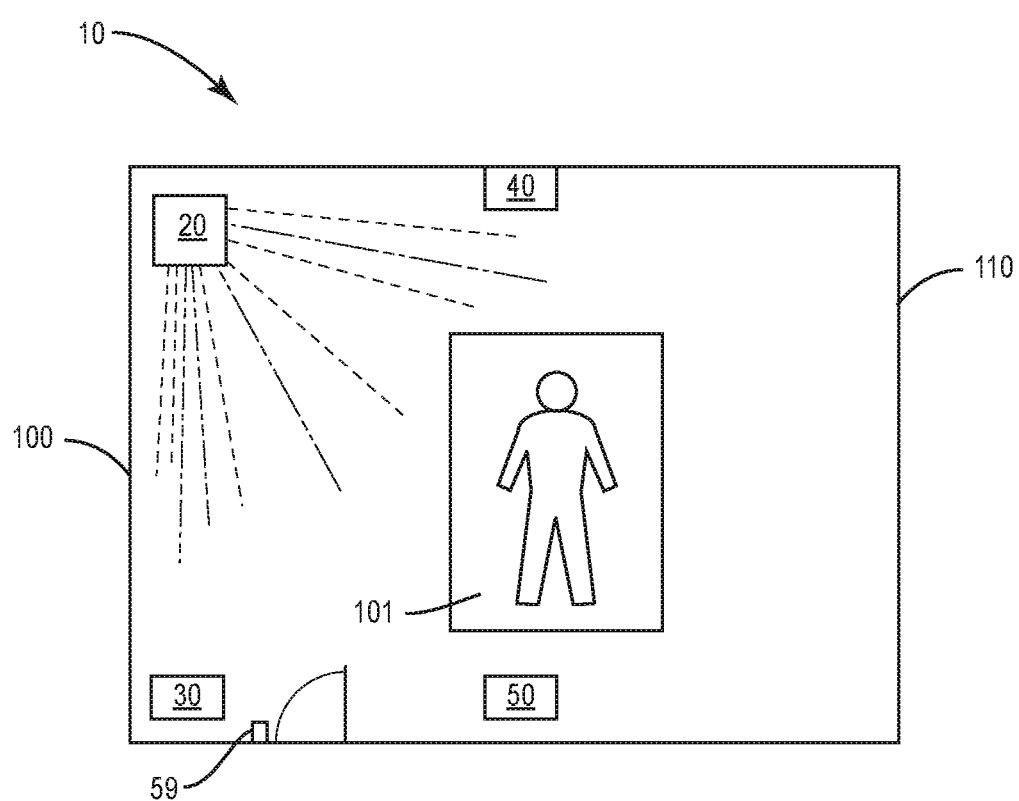
FIG. 1 is a schematic view of a system relative to an environment that includes a single section.

FIG. 1 illustrates a schematic diagram of a disinfection system 10. The system 10 is designed for use with a predetermined environment 100. The system tracks one or more persons in the environment 100 and includes a germicidal radiation emitter 20 configured to emit germicidal radiation within the environment 100. The germicidal radiation may include one or more of UV-C, UV-B, and HINS radiation. A sensor 30 is configured to detect that the person is within the environment 100 and possibly also their location in the environment 100. Sensor 40 is configured to detect whether the person(s) detected in the environment 100 is equipped with eye protection. Sensors 30 and 40 could be a single sensor that detects both the presence of a person and whether or not they are equipped with eye protection. Processing circuitry 51 within a computing device 50 receives signals from the sensors 30, 40 and operates the emitter 20 accordingly. Although FIG. 1 includes a single emitter 20, sensor 30, sensor 40, and computing device 50, the system 10 may include one or more of any of the various system components.

Different amounts of germicidal radiation may be emitted by the system 10. In a section of the environment 100 where the person is not located, the emitter 20 emits a first amount of germicidal radiation. In the section where the person is located, the emitter 20 operates in a different second mode and emits a second amount of germicidal radiation. If the person has protective equipment, the amount of germicidal radiation may be greater than if the person does not have protective equipment. Furthermore, if there are not persons in the environment, the emitters may be set to increase the amount of germicidal radiation emitted for a more thorough decontamination of the area, and alternatively decrease the emitted radiation after a prescribed period of time to save energy, extend emitter life, and minimize UV damage to surfaces in the environment. In addition, since the presence of persons introduce or stir up microorganisms that have settled out on surfaces, the emitters may be set to increase the levels of germicidal radiation emitted when persons enter the area, provided sensors 30 and 40 detect that all persons in the area have PPE.

The processing circuitry 51 may be configured to receive signals from one or more of the sensors 30 to determine the number of people within the environment. Based on this information, the system adjusts the germicidal radiation emitted into the environment proportional to the number. For example, the emitted germicidal radiation may be set to a first level when the system detects a single person in the environment. The emitted germicidal radiation may then be increased to a second level when the system detects three people in the environment.

Similarly, the processing circuitry 51 may receive signals from one or more of the sensors 30 to detect motion of the one or more people in the environment. This activity monitoring may be used to adjust the emitted germicidal radiation. Germicidal radiation may be increased during times of higher activity such as coughing or sneezing or walking around the room. The germicidal radiation may be decreased during times of lower activity such as a single person that is sleeping or watching television.

The disinfection system 10 is particularly applicable to a medical facility, such as a hospital, doctor's office, nurse's station, etc. The system 10 is also applicable to other settings, such as schools, office buildings, retail stores, shopping centers, nursing homes, rehabilitation facilities, biological research facilities, food preparation facilities, private homes, and various other locations and populated environments that are susceptible to the existence of microorganisms that cause illness.

FIG. 1 and the following discussion include a system 10 that tracks one or more persons in the environment 100. Further, the system 10 may include one or more of any of the various system components including an emitter 20, person sensor 30, protective equipment sensor 40, and computing device 50. Further, sensors 30, 40 may be combined into a single component.

Figure 2:
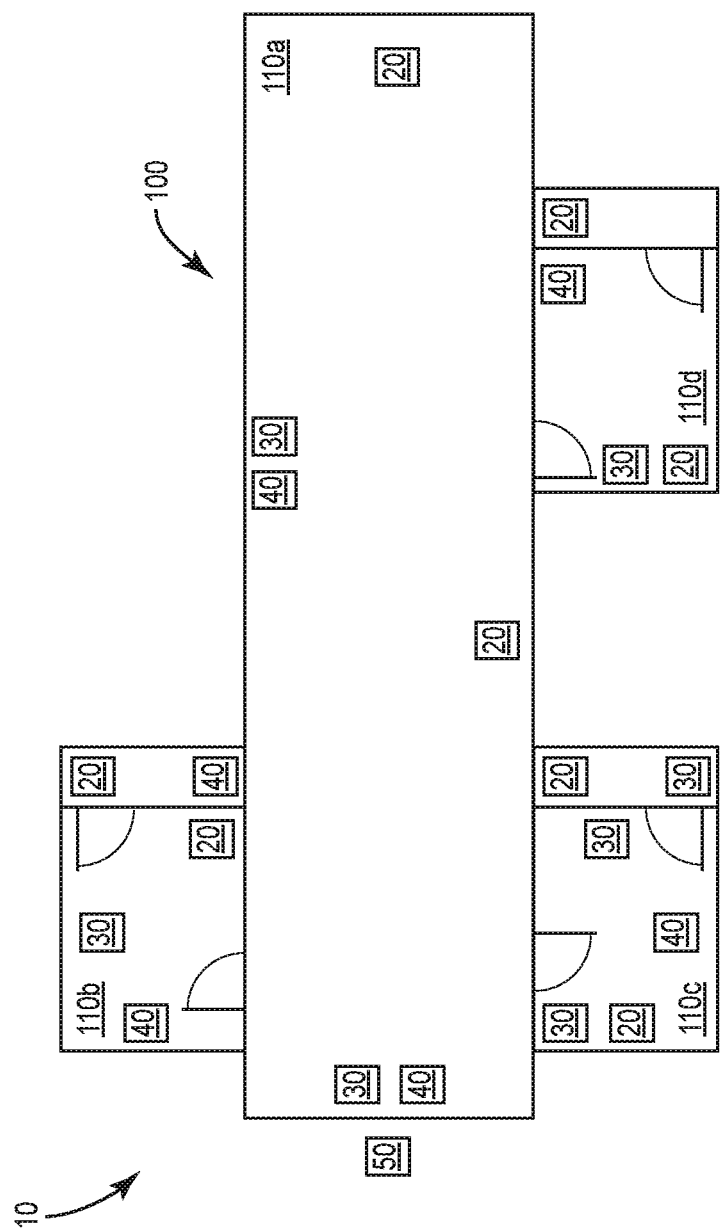
FIG. 2 is a schematic view of a system relative to an environment that includes multiple sections.

FIG. 1 includes the environment 100 being a single room, such as a hospital room or operating room of a medical facility. The system 10 is also applicable for operating in a wide variety of environments having various shapes and sizes. Examples include an environment with multiple rooms, an entire hospital wing, a hospital floor, an entire hospital, an office or office building, a cafeteria of a school with multiple rooms, and an entire school. FIG. 2 illustrates the system 10 within a larger environment 100 that include four sections 110a-110d. Further, rooms 110b-d include two independent rooms (such as a hospital room with an adjoining bathroom). One example of such an environment is a hospital wing that includes a main hallway (such as section 110a) and separate patient rooms (sections 110b-d).

Each germicidal emitter 20 is configured to emit germicidal radiation, typically ultraviolet radiation in the ultraviolet electromagnetic radiation range. This range is generally considered to be electromagnetic radiation of a wavelength between approximately 100 nm-400 nm. Peak effectiveness for germicidal radiation as a disinfectant is between wavelengths of approximately 240 nm and approximately 300 nm. Germicidal radiation between these wavelengths may destroy DNA in living microorganisms found in the air, on surfaces, and in liquids in an indoor environment. Examples of micro-organisms that may be treated by the system 10 include but are not limited to bacteria, viruses, and fungi.

A variety of different germicidal emitters 20 may be used in the system 10 of any size and shape and can include emitters which emit continuous germicidal radiation or intermittent or pulsed germicidal radiation, sometimes referred to flashtubes or flashlamps. The emitter 20 may include a high intensity discharge lamp (also called high pressure or medium pressure mercury vapor lamps) and low pressure mercury vapor lamps. The emitter 20 may include PUV xenon lamps (pulsed high power xenon lamps producing broad spectrum 100-1000 nm light with a high UV-C component), and excimer lamps. Discharge lamps are lamps that generate germicidal radiation by means of an internal electrical discharge between electrodes in the presence of a gas. The term encompasses gas discharge lamps, which generate germicidal radiation by sending an electrical discharge through an ionized gas, and surface discharge lamps, which generate germicidal radiation by sending an electrical discharge along a dielectric surface in the presences of a gas, producing a plasma along the substrate's surface. Discharge lamps may be further characterized by the type of gas or gases used and the pressure at which they are operated. The discharge lamps may be low pressure, medium pressure, or high intensity. The gases may include but are not limited to helium, neon, argon, krypton, xenon, nitrogen, oxygen, hydrogen, water vapor, carbon dioxide, mercury vapor, sodium vapor, or combinations thereof.

A commonly used gas-discharge lamp used to produce continuous light is a mercury-vapor discharge lamp, which emits a strong peak of 253.7 nm radiation, which is particularly effective for use in germicidal disinfection. Another commonly used UV lamp for germicidal disinfection is a xenon flashtube, which emits a broad spectrum of UV light in the entire spectrum known to be germicidal (both UV-C and UV-B, between approximately 200 nm and 320 nm). The combination of multiple wavelengths is more effective against some micro-organisms due to the ability of some microorganisms to repair damaged DNA from single wavelength UV radiation but not multiple wavelengths due to the fact that different UV wavelengths create different types of photo-initiated damage to the DNA that make it less probable that the organism can repair all types of damage simultaneously. Low pressure mercury vapor lamps emit almost exclusively UV-C radiation. Emitter 20 may also be an ultraviolet light emitting diode (UV LED). A UV LED emitter 20 may be configured to emit a narrow band of UV-C radiation at almost exactly the peak of germicidal effectiveness. A UV LED emitter 20 includes LED's that may include various configurations, such as a standard bulb type LED, a flat circle LED, and a rectangle LED. The UV LED emitter 20 may include a bank of LED's. The LED's may be mounted in a single bank of LED's or strips of LED's that each includes multiple LED's. Specific embodiments may include LED's mounted in a relatively flat arrangement or in strips, or rectangular arrays such as a picture frame and hung on walls or on the backs of doors. The UV emitter 20 may be combinations of any of these aforementioned UV emitters. The emitter 20 may also be a plasma arc flash. The UV emitter 20 may be multiple emitters of the same or different types.

The emitter 20 may also be a High Intensity Narrow Spectrum (HINS) emitter, which typically is constructed of LED's emitting visible light in the violet and blue light range between 380 and 420 nm, usually centered on 405 nm.

The germicidal emitter 20 may also be a laser; multiple types of lasers and emitters could be considered that emit wavelengths of radiation with germicidal properties. For example, excimer lasers (e.g. ArF at 193 nm, KrCl at 222 nm, KrF at 248 nm, XeCl at 308 nm, etc.), Nd:YAG lasers (e.g. 5th harmonic at 213 nm, 4th harmonic at 266 nm, etc.), He-Ag+ (224.3 nm), Ne-Cu+ (248-270 nm), He-Au+ (282-292 nm), Ti:sapphire (tripled, 235-330 nm), or any combinations of these and other germicidal wavelength emitting lasers in the 190-430 nm range could be used.

In some embodiments it is desirable that the germicidal radiation source 20 produce a direction and intensity controlled beam of germicidal radiation. A direction and intensity controlled beam of radiation is radiation that can be directed towards certain areas in the environment, such as the light that is produced from a laser or a spot light, rather than light that is broadly diffused throughout the environment. Lasers naturally produce this type of beam with very little diffusion, but the radiation output of other germicidal radiation sources (e.g. discharge lamps, LED's, etc.) can be collected and channeled into a narrow beam of non-diffuse light by means known in the art. Such means can include mirrored cavities and surfaces specifically designed to contain and channel radiation to a single narrow opening. Non-imaging or anidolic optical devices (e.g. light tubes, light guides, non-imaging reflectors and lenses) and fiber optics have also been used to create a direction controlled beam of radiation from a diffuse light source. Aluminum coatings are particularly effective for containing and directing UVC and UVB radiation. One commercial example of a device that can produce a very narrow beam of direction controlled radiation from both diffuse and non-diffuse sources is the DLP (Digital Light Processing) projection technology originally developed at Texas Instruments. This technology is said to be "light source agnostic" and can use a high-pressure xenon arc lamp generating diffuse light from a quartz arc tube or an LED that is shaped into a very narrow beam of direction controlled radiation using mirrored surfaces and non-imaging optical devices. Lasers are also suitable emitters for the DLP technology without the need for collecting and shaping the light into a narrow beam with non-imaging optical devices.

The emitters 20 are operatively connected to the processing circuitry 51 to operate in different modes that emit different amounts of germicidal radiation. A first mode may emit a higher amount of germicidal radiation than a second mode. The first mode may be used in sections of the environment 100 where the person is not located (i.e., unoccupied sections). The second mode may be used in sections where the person is located. The emitters 20 may also operate in intermediate modes of operation that emit amounts of germicidal radiation between that of the first and second modes. The intermediate modes may be used in various contexts, such as for a section that includes a person with protective equipment.

The different emitters 20 may be automatically adjusted by the processing circuitry 51 in a number of different manners. One manner of varying the amount of ultraviolet radiation or HINS light includes adjusting the number of lamps or LED's that are activated in a multi-lamp or multi-LED emitter 20. By way of example, a three-lamp emitter 20 may operate in the first mode with each of the lamps activated and the second mode with just one of the lamps activated. An intermediate mode may include two lamps activated. A multi-lamp emitter 20 may also include lamps that emit different amounts of germicidal radiation. A first mode may include one or more of the lamps activated thus producing the first amount of germicidal radiation, and a second mode includes a different combination of lamp activation that produces a second amount.

The emitters 20 may also be adjusted by controlling the electrical parameters (voltage, current, etc.).

The emitters 20 may also include covers capable of blocking some or all of the emitted radiation. The covers may be adjustable to control the output. This may include the lamps being uncovered when operating in a higher mode and one or more of the lamps being partially or completely covered in a lower mode. The covers may include multiple different sections that may be moved relative to the lamps. In a first mode, a first cover extends over one or more of the lamps resulting in the emitter 20 emitting a first amount of germicidal radiation. A second cover extends over the one or more lamps in a lower mode resulting in a lower amount of germicidal radiation. In one specific embodiment, the covers include louvers that are formed of an opaque material that prevents the passage of germicidal radiation. The louvers are movable between an open position to allow the passage of germicidal radiation from the emitter 20 to the environment 100, a closed position that blocks the passage of germicidal radiation, and various intermediate positions.

The emitters 20 may be configured to be interchangeable with existing fluorescent light fixtures. In one embodiment, ultraviolet lamps can be plugged into existing fluorescent lamp fixtures. This would be very advantageous in that it may save money in some installations.

The emitters 20 may emit a relatively constant amount of germicidal radiation over a period of time. Alternatively, the emitters 20 may be pulsed to emit a relatively high level of radiation for a first time period, followed by lower radiation or no radiation for a second time period. The pulsed bursts may emit more intense amounts of germicidal radiation than a continuous emission, but for a shorter duration. The length of the time periods may vary depending upon the desired extent of germicidal radiation that is to be emitted into the environment 100.

The emitters 20 may include visual indicators to allow any person to visually determine whether or not germicidal radiation is being emitted. For example, a red or green light may be used to indicate whether the emitter 20 is on, or covers could move to cover the emitter(s) 20 when it is off, giving immediate, positive confirmation that the environment is safe to remove protective equipment.

Ultraviolet radiation has been found to be one way to treat environments (including but not limited to rooms, surfaces, air, and liquids in the environment) to reduce the level of micro-organisms. Ultraviolet germicidal irradiation is a disinfection method that uses electromagnetic ultraviolet radiation at a sufficiently short wavelength to break down these micro-organisms. The relatively short wavelength of ultraviolet-C and B radiation is harmful to forms of life at the micro-organic level because it destroys the organism's ability to reproduce by causing photochemical reactions in the nucleic acids in their DNA and/or RNA chemical structure. This disruption prevents micro-organisms from replicating, thereby rendering them inactive and unable to cause infection.

Certain wavelengths of germicidal radiation cause photochemical reactions and are effective for germicidal purposes. Ultraviolet-C radiation with a wavelength of between 180-280 nm (and particularly between 240 nm-280 nm) has been found to be particularly effective, as well as ultraviolet-B radiation with a wavelength between 280-320 nm. Conversely, UVA radiation between 320-400 nm has fewer germicidal benefits, and therefore germicidal radiation is contained in the UVC and UVB bands. More recently, other wavelengths of radiation in the visible range have been found to have germicidal activity. High intensity narrow spectrum light (HINS) in the range of 380 to 420 nm, violet light, and particularly the 400-410 nm range centered on 405 nm, has been found to have some germicidal activity.

The term "germicidal" implies the radiation destroys, kills, or inactivates microorganisms such as viruses, bacteria, and fungi (viruses are molecules, and so it is customary to refer to viruses as being inactivated rather than killed). In the present application, the term "disinfecting", "disinfection", and the like includes germicidal action that reduces a microbial population, as well as germicidal action that eliminates a microbial population.

Safe levels of germicidal radiation exposure have been calculated. In the United States, ACGIH has established a limit of 30 J/m$^2$/day for exposure to germicidal radiation between 180 and 400 nm if the exact wavelength(s) of radiation being emitted is not known. If the exact wavelengths of radiation being emitted are known, then the allowable exposure limits are established by the limits defined in Table 1. Note that Table 1 adopts the current convention in which UVB is defined as 280-320 nm and UVA is defined as 320-400 nm. Exposure levels above these limits are considered unsafe for humans who are not wearing eye or skin protection, while levels at or below these limits are considered safe for humans and have been found to cause fewer safety concerns.

TABLE 1

UV Exposure Limits and Spectral Weighting Functions

| Band | Wavelength, nm | Relative Spectral Effectiveness | Exposure Limit, J/m2 |
|---|---|---|---|
| UVC | 180 | 0.012 | 2500 |
| | 190 | 0.019 | 1600 |
| | 200 | 0.03 | 1000 |
| | 205 | 0.051 | 590 |
| | 210 | 0.075 | 400 |
| | 215 | 0.095 | 320 |
| | 220 | 0.12 | 250 |
| | 225 | 0.15 | 200 |
| | 230 | 0.19 | 160 |
| | 235 | 0.24 | 130 |
| | 240 | 0.3 | 100 |
| | 245 | 0.36 | 83 |
| | 250 | 0.43 | 70 |
| | 254 | 0.5 | 60 |
| | 255 | 0.52 | 58 |
| | 260 | 0.65 | 46 |
| | 265 | 0.81 | 37 |
| | 270 | 1 | 30 |
| | 275 | 0.96 | 31 |
| | 280 | 0.88 | 34 |
| UVB | 280 | 0.88 | 34 |
| | 285 | 0.77 | 39 |
| | 290 | 0.64 | 47 |
| | 295 | 0.54 | 56 |
| | 297 | 0.46 | 65 |
| | 300 | 0.3 | 100 |
| | 303 | 0.19 | 250 |
| | 305 | 0.06 | 500 |
| | 308 | 0.026 | 1200 |
| | 310 | 0.015 | 2000 |
| | 313 | 0.006 | 5000 |
| | 315 | 0.003 | 10000 |
| | 316 | 0.0024 | 13000 |
| | 317 | 0.002 | 15000 |
| | 318 | 0.0016 | 19000 |
| | 319 | 0.0012 | 25000 |

TABLE 1-continued

UV Exposure Limits and Spectral Weighting Functions

| Band | Wavelength, nm | Relative Spectral Effectiveness | Exposure Limit, J/m2 |
|---|---|---|---|
|  | 320 | 0.001 | 29000 |
| UVA | 320 | 0.001 | 29000 |
|  | 322 | 0.00067 | 45000 |
|  | 323 | 0.00054 | 56000 |
|  | 325 | 0.0005 | 60000 |
|  | 328 | 0.00044 | 68000 |
|  | 330 | 0.00041 | 73000 |
|  | 333 | 0.00037 | 81000 |
|  | 335 | 0.00034 | 88000 |
|  | 340 | 0.00028 | 110000 |
|  | 345 | 0.00024 | 130000 |
|  | 350 | 0.0002 | 150000 |
|  | 355 | 0.00016 | 190000 |
|  | 360 | 0.00013 | 230000 |
|  | 365 | 0.00011 | 270000 |
|  | 370 | 0.000093 | 320000 |
|  | 375 | 0.000077 | 390000 |
|  | 380 | 0.000064 | 470000 |
|  | 385 | 0.000053 | 570000 |
|  | 390 | 0.000044 | 680000 |
|  | 395 | 0.000036 | 830000 |
|  | 400 | 0.00003 | 1000000 |

Safe levels of UV radiation exposure have been calculated. In the United States, ACGIH has established a limit for exposure to UV radiation between 180 and 400 nm. The ACGIH threshold limit value (TLV) for UV is harmonized with the International Commission on Non-Ionizing Radiation Protection (ICNIRP) guidelines. Under these guidelines for broadband sources, the UV incident on the eye must be weighted by a relative spectral effectiveness function to obtain the "effective irradiance". The tabulated values for this weighting function can be found in the ACGIH TLV booklet or the ICNIRP guideline for UV. The integral of the effective irradiance over time (or, for constant irradiance, the product of effective irradiance and exposure time) shall not exceed 3 mJ/cm$^2$ in a day. If the effective irradiance varies over time, the 3 mJ/cm$^2$ limit should be applied to the effective radiant exposure, which can be measured using an integrating UV radiometer. The exposure limits may vary from country to country and should be reviewed for the standards that apply to each installation.

For the purposes of this application, "adequate" protection from germicidal radiation is defined as a level of protection that will protect a person in the environment such that they are not exposed to unsafe levels of germicidal radiation (i.e., levels of exposure that do not exceed government or medical allowed levels). For example detecting whether or not eye protection being worn is "adequate" means that it is capable of blocking UV light such that the cumulative dose of UV light falling on the person's eyes does not exceed the threshold limit value for an 8 hour period. To ensure adequacy of protection, sensors 30 can be positioned inside the protective eyewear to monitor UV light getting through the eyewear to the eye. Likewise, sensors 30 can be worn on the skin, even under the blocking creams or lotions, to determine the adequacy of the measures used to protect the skin.

The system 10 further includes one or more sensors 30 for detecting the presence of persons and location of the person within the environment 100. The sensors 30 may be operable to detect any one of or combinations of a variety of parameters, such as motion, heat, sound, reflected or transmitted light, or the like. The sensors 30 may include various types of sensing technology, including but not limited to motion or movement sensing, image capture and video monitoring, RFID's, thermal or infrared sensing and imaging, microphones, sonic or ultrasonic transducers, lasers, light-emitting diodes (LEDs), photodetectors, and photoresistors. The sensors 30 may be detect the presence of a person in the environment 100, and optionally their location within the environment.

The environment 100 may also be equipped with sensors 30 to track the location of the person in the environment. This may include sensors 30 on the doors within the environment that can detect opening/closing. Input devices 59, such as card readers, keyboards, etc. may also be located about the environment. The input devices 59 require that the person enter required information such as a passcode or card swipe in order to enter the environment 100, or sections 110 of the environment 100.

The system 10 may also assign RFID tags to the person, such as tags incorporated into a wrist band. RFID readers 30 are positioned in the environment 100 to read the electronic information stored on the tag to determine the location of the person in the environment.

The system 10 may be configured with one or more sensors 30 to detect the presence and position of the person in the environment. When multiple sensors 30 are used, the sensors 30 may be the same or different. The system may include multiple sensors and/or multiple wireless technologies to triangulate the position of individuals, which is needed for more accurate position measurements.

In one embodiment, a network of video monitoring cameras coupled with a computer vision software application such as Microsoft's Kinect, may be useful to track persons in an environment. Kinect is typically used in conjunction with Apple's Primesense camera to capture images of persons in the environment. Using Kinect programming, real time tracking of persons in the environment and their body movements is possible.

The system 10 also includes one or more sensors 40 for detecting that protective equipment is being used by each of the persons in the environment 100. These sensors 40 may be on the protective equipment or may be positioned away from the protective equipment.

Figure 3:
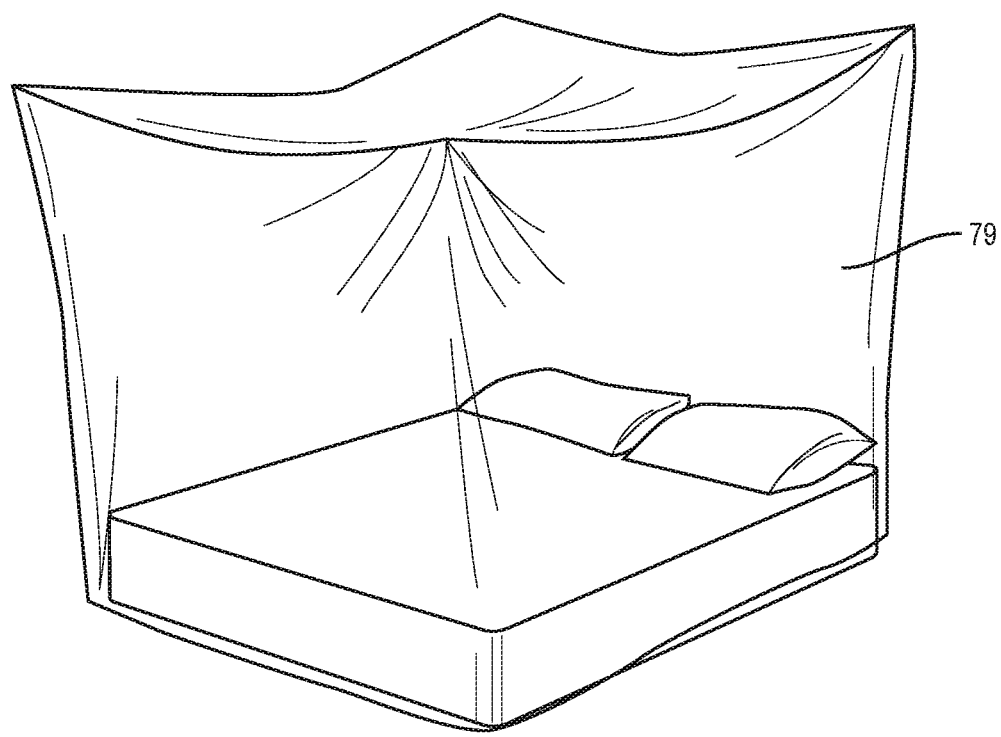
FIG. 3 is a perspective view of a protective tent that extends around a bed.

A variety of different protective equipment may be used and detected by the processing circuitry 51. This may include equipment that shields a user from the germicidal radiation but is not worn, such as but not limited to blankets that extend over a person laying in a bed, and a tent that extends around a particular location in a room (e.g., around a bed). FIG. 3 illustrates an embodiment with a protective tent 79 that extends around a patient bed. The protective tent 79 is constructed from a material that prevents or reduces passage of germicidal radiation. Thus, a patient within the tent 79 is not exposed to the same levels of germicidal radiation as if they were outside.

Figure 4B:
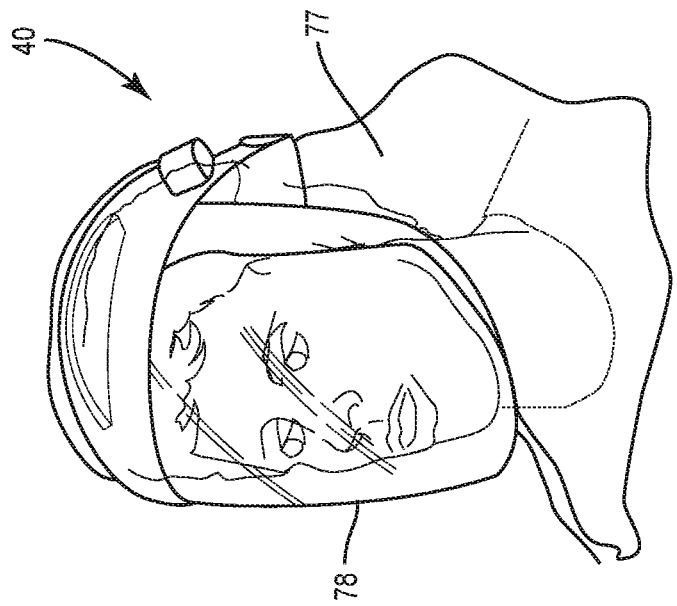
FIG. 4B is a perspective schematic view of a person wearing protective equipment.
Figure 4A:
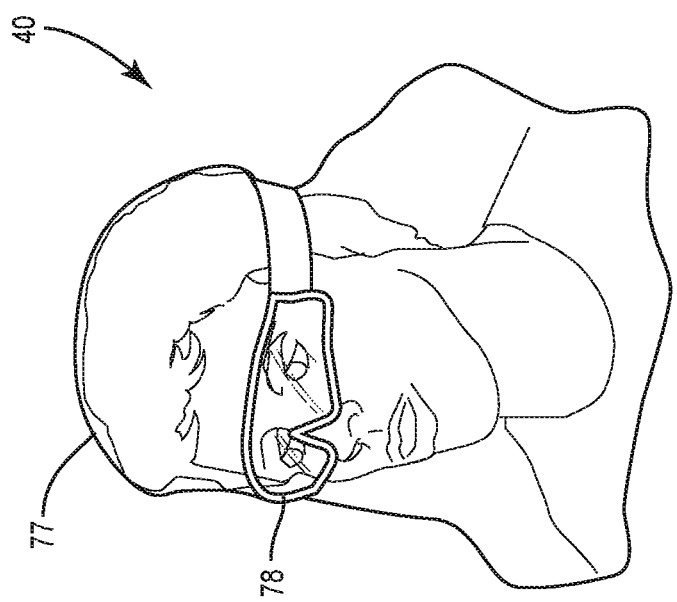
FIG. 4A is a perspective schematic view of a person wearing protective equipment.

The eye protection may also include equipment that is worn by the user such as but not limited to eyewear (goggles, glasses, night shade, etc.), lotion, head shield, and clothing (long sleeved shirts, gloves, neck covers, face masks, socks, hats, etc.). FIGS. 4A and 4B include eye protection 40 that is worn by a person and includes a first transparent section 78 that extends over the person's eyes, and a second section 77 constructed from a flexible material, such as fabric or sheet-like material sized to extend over the person's face, head, and/or neck. The transparent section 78 may include a single continuous piece that extends over both eyes, such as a visor, face shield, or face mask, or may include separate pieces that each extend over one eye such as glasses.

The eye protection that shields a user may be equipped with switches and/or sensors and the like that detect the location of the eye protection and whether or not it is positioned in a way that signifies whether or not the user is adequately protected. When the eye protection is in the proper location on the user, the switches or sensors are activated indicating proper use to protect the user. When the eye protection is improperly positioned or not in use, the switch(s) and/or sensors remain open or closed or in an "unsatisfied" condition or state that indicates the eye protection is not properly positioned. The processing circuitry 51 monitors the switches and/or sensors to determine use of the eye protection.

Other ways to detect the use of this type of protective eye protection include visual monitoring systems coupled with human or computer analyses of the images. Still another way of detecting whether each person in the environment has adequate eye protection is to place detecting sensors on the inside of the eyewear, in proximity to the eye; if the eye protection comes off the face and germicidal radiation is present in the environment, the sensor detects the germicidal radiation and sends a signal to the controller so appropriate action can be taken to decrease the emitters into a safer mode of operation, including turning the emitters completely off.

Equipment that is worn by the user may be detected in different manners. In one embodiment, each person that enters the environment 100 is equipped with a communication unit. The unit includes control circuits that include one or more programmable processors and associated control software. The communication unit also includes one or more receivers or transceivers, such as one or more RFID signal receivers, RF transceivers of various types which could include cellular-type interfaces all without limitation. The RFID signal receivers can receive information from identifiers, such as RFID sensors, or tags, which are associated with the various protective equipment that are worn by the person. The communication unit periodically polls for the existence of the identifiers. If the unit does not receive a signal from the identifier, the unit communicates with the processing circuitry 51 thus indicating that the protective equipment is not being worn.

Various types of protective eyewear can be used with the system. Examples include glasses (preferably with side shields or wrap-around style), goggles, and face shields. Contacts with additives capable of blocking germicidal radiation could also be used. Polycarbonate is a material that is widely used for blocking UV light, since additives (dyes) can be added to give 99.9% blockage of UV between 180 and 400 nm (this range encompasses UVA, UVB, and UVC); various types of UV-blocking eye protection are commercially available. Protective eyewear that shields against HINS light can include eyewear made of materials transparent to longer wavelengths of visible light but which block violet and blue wavelengths; various types of blue and violet-blocking eye protection are commercially available.

The sensor 40 may also be configured to detect for exposed skin on the person. Sensor 40 may include an infrared detection that is signaled to the processing circuitry 51 that calculates the temperature of any exposed skin. Based on the detected temperature, the processing circuitry 51 detects whether the person is wearing equipment such as clothing or lotion. The protective equipment results in a lower skin temperature.

Sensor 40 may also be configured to detect data indicative of a color of the user's skin. Lotions that are to be applied by the person may be colored which can be detected by the sensor 40. For example, the lotion may include white pigments that provide a high visual indication when worn by the person. The lotion may also include a fluorescent marker or dye, preferably a marker or dye that is invisible to the human eye that causes the skin to have a different visual appearance when viewed by the sensor 40. In one embodiment, these materials cause the skin to "glow" when the materials are exposed to germicidal radiation, thereby making them more amenable to analysis by humans or computer algorithms. The detected information from the environment is sent to the processing circuitry 51 that processes the data and is able to differentiate bare skin (i.e., unprotected skin) from that with lotion or other protection (e.g., clothing). In another embodiment, this fluorescent marker is useful to assist the human inspection of creams or lotions applied to the skin. The nurse or patient applies the cream, then views the skin through a monitor, possibly even a hand held device such as an iPad, where as a result of computer image enhancement areas of the skin that are not adequately covered by germicidal radiation screening coatings immediately stand out and become obvious to the person applying the cream. The process can then be repeated until the desired result of complete coverage is obtained. This process of monitoring can be repeated as often as deemed necessary and the screening coatings reapplied to ensure the safety of those in the environment. In another embodiment, biocidal additives that are capable of killing microorganisms can also be added to the skin creams, lotions, or coatings along with the pigments or dyes to further reduce microorganism populations directly on the skin of the persons in the environment. This combination of germicidal radiation plus biocidal skin coatings can greatly enhance the destruction of microorganisms in the immediate environment of persons and on the persons themselves, something no other system is able to provide on a continuous basis.

In one embodiment, the processing circuitry 51 determines in a binary manner whether the person is wearing protective equipment. If the person is wearing the protection, the processing circuitry 51 operates in a particular manner and emits a particular amount of germicidal radiation. If the person is not wearing protection, the processing circuitry 51 operates in a different manner and emits a lesser amount of germicidal radiation, including no radiation. The processing circuitry 51 may also be configured to determine intermediate degrees of protection. For example, the processing circuitry 51 may detect an amount of lotion that is applied on the skin based on the detected temperature and/or skin coloring. The processing circuitry 51 may then operate in one of the modes that is applicable to the extent of personal protection that is detected.

Figure 5A:
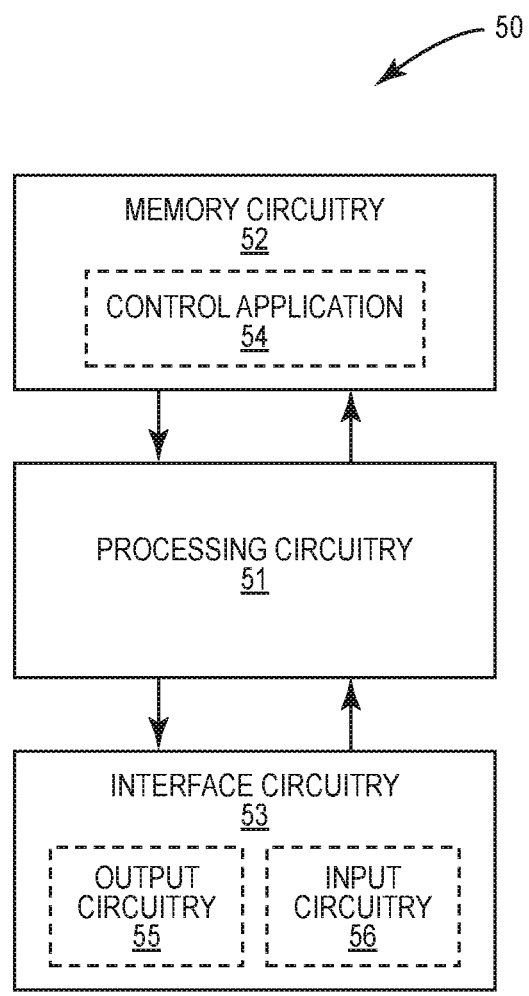
FIG. 5A is a schematic diagram of a computing device.

Other embodiments of the present disclosure include the computing device 50 implemented according to the hardware illustrated in FIG. 5A. The example hardware of FIG. 5A comprises processing circuitry 51, memory circuitry 52, and interface circuitry 53. Additional components such as the one or more sensors 30, 40, one or more emitters 20, clock 56, display 58, and input device 59 are configured to communicate with the computing device 50 through the interface circuitry 53.

The processing circuitry 51 is communicatively coupled to the memory circuitry 52 and the interface circuitry 53, e.g., via one or more buses. The processing circuitry 51 may comprise one or more microprocessors, microcontrollers, hardware circuits, discrete logic circuits, hardware registers, digital signal processors (DSPs), field-programmable gate arrays (FPGAs), application-specific integrated circuits (ASICs), or a combination thereof. For example, the processing circuitry 51 may be programmable hardware capable of executing software instructions stored as a machine-readable computer program 54 in the memory circuitry 52. The memory circuitry 52 of the various embodiments may comprise any non-transitory machine-readable media known in the art or that may be developed, whether volatile or non-volatile, including but not limited to solid state media (e.g., SRAM, DRAM, DDRAM, ROM, PROM, EPROM, flash memory, solid state drive, etc.), removable storage devices (e.g., Secure Digital (SD) card, miniSD card, microSD card, memory stick, thumb-drive, USB flash drive, ROM cartridge, Universal Media Disc), fixed drive (e.g., magnetic hard disk drive), or the like, wholly or in any combination.

The interface circuitry 53 may be a controller hub configured to control the input and output (I/O) data paths of the computing device 50. Such I/O data paths may include data paths for exchanging signals over a communications network and data paths for exchanging signals with a user. For example, the interface circuitry 53 may comprise a transceiver configured to send and receive communication signals over one or more of a cellular network, Ethernet network, or optical network. The interface circuitry 53 may also comprise one or more of a graphics adapter, display port, video bus, touchscreen, graphical processing unit (GPU), display port, Liquid Crystal Display (LCD), and Light Emitting Diode (LED) display, for presenting visual information to a user. The interface circuitry 53 may also comprise one or more of a pointing device (e.g., a mouse, stylus, touchpad, trackball, pointing stick, joystick), touchscreen, microphone for speech input, optical sensor for optical recognition of gestures, and keyboard for text entry.

The interface circuitry 53 may be implemented as a unitary physical component, or as a plurality of physical components that are contiguously or separately arranged, any of which may be communicatively coupled to any other, or may communicate with any other via the processing circuitry 51. For example, the interface circuitry 53 may comprise output circuitry 55 (e.g., transmitter circuitry configured to send communication signals over the communications network) and input circuitry 56 (e.g., receiver circuitry configured to receive communication signals over the communications network). Similarly, the output circuitry 55 may comprise a display, whereas the input circuitry 56 may comprise a keyboard. Other examples, permutations, and arrangements of the above and their equivalents will be readily apparent to those of ordinary skill.

According to embodiments of the hardware illustrated in FIG. 5A, the interface circuitry 51 is configured to receive signals from one or more sensors 30, 40. The processing circuitry 51 is configured to receive the signals and determine various aspects regarding the environment. This may include but is not limited to the processing circuitry 51 configured to perform calculations to determine various aspects such as but not limited to the skin temperature of a person, skin color, the number of people within the environment 100, the time each person has been in the environment, where within the environment each person has been, the use of protective equipment such as eye protection, the level of radiation emitted, and the amount of time that each emitter 20 has been activated.

Interface circuitry 53 may also provide communications with one or more of the emitters 20. Signaling between the interface circuitry 53 and the emitter(s) 20 provides for the processing circuitry 51 of the computing device 50 to control the amount of germicidal radiation that is being emitted into the environment 100.

Figure 5B:
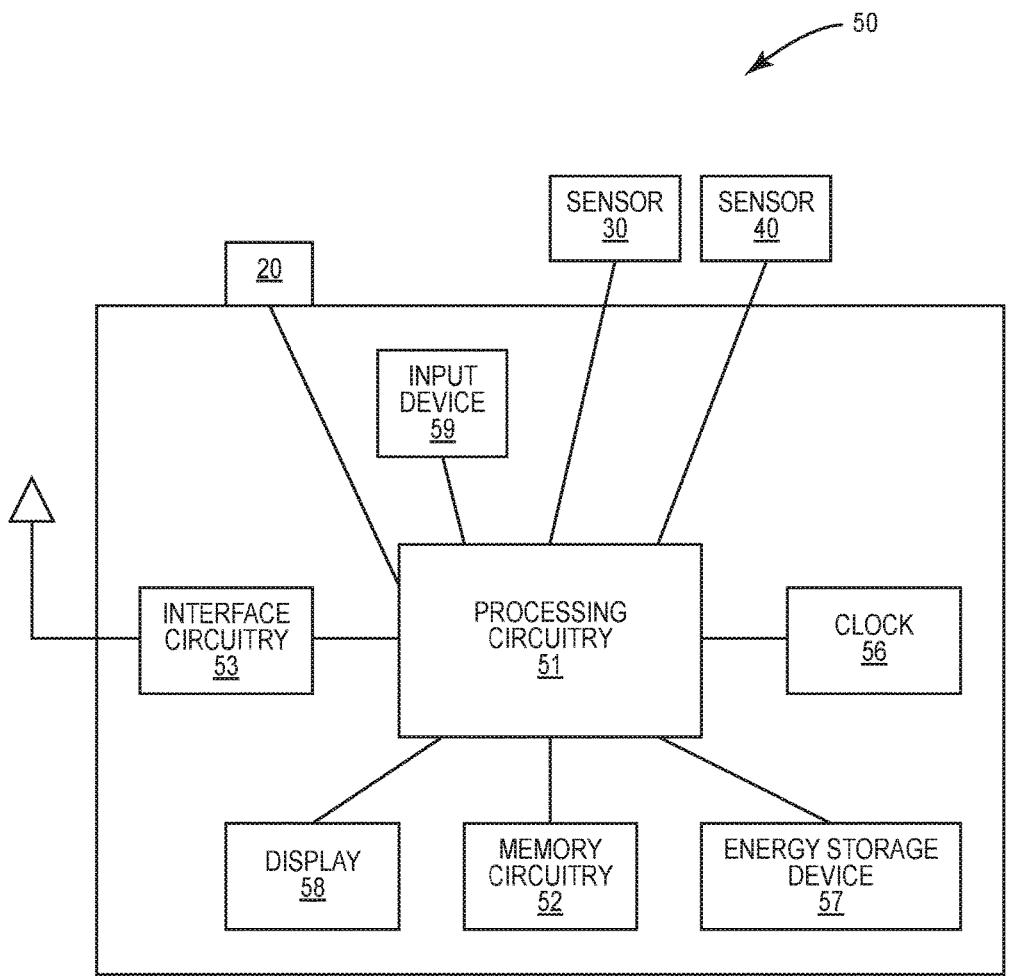
FIG. 5B is a schematic diagram of a computing device.

Other embodiments of the present disclosure include the computing device 50 as illustrated in FIG. 5B. The computing device 50 controls the operation of the system 10. As illustrated in FIG. 5B, the computing device 50 includes processing circuitry 51 that includes, for example, one or more microprocessors, microcontrollers, Application Specific Integrated Circuits (ASICs) or the like, configured with appropriate software and/or firmware to control the overall operation of the system 10 according to program instructions stored in the memory circuitry 52. The processing circuitry 51 is configured to perform calculations to determine various aspects such as but not limited to the skin temperature of a person, skin color, the number of people within the environment 100, the time each person has been in the environment, where within the environment each person has been, the use of eye protection, the level of radiation emitted from the one or more emitters 20, and the amount of time that each emitter 20 has been activated.

The computing device 50 includes a computer-readable storage medium (shown as memory circuitry 52), which stores instructions and/or data needed for operation. The memory circuitry 52 may include both volatile and non-volatile memory, for example.

The computing device 50 receives signals from various sources such as the one or more sensors 30, 40 regarding people within the environment 100 and protective equipment. The sensors 30, 40 may be separate components that are communicatively coupled to the computing device 50 as illustrated in FIG. 5B. Other embodiments may include the sensors 30, 40 included within the processing circuitry 51.

The interface circuitry 54 may comprise a short-range wireless interface, such as a BLUETOOTH interface, RFID, ZIGBEE, or WIFI interface, and a long range cellular phone or satellite communications interface. Interface circuitry 54 may also include an antenna configured for transmitting and receiving wireless signals to and from remote sources. The interface circuitry 54 may also be equipped to wirelessly communicate with the components within the environment such as sensors 30, 40, and emitter(s) 20.

A clock 56 may be associated with the computing device 50 that measures the various timing requirements for specific events. The clock 56 may be independent from the processing circuitry 51 as illustrated in FIG. 5B, or may be incorporated within the processing circuitry 51. Clock 56 may interface through the interface circuitry 53 (see FIG. 5A).

An energy storage device 57 (e.g., a battery) is provided to power the various components of the computing device 50, such as the processing circuitry 51. In one embodiment, the energy storage device 57 is a battery. One or more of the components may also be configured to be wired into the power supply of the environment 100 in which it is mounted.

A display 58 may be configured to display information to a person or someone monitoring the system 10. The display 58 may comprise a liquid crystal display (LCD) or an organic light emitting diode (OLED) for example. An input 59 may provide for the input of information, such as a person entering into the environment 100 to enter identification. The input 59 may include a variety of formats, including but not limited to one or more buttons, touchpad, and keypad. The display 58 and/or the input 59 may interface through the interface circuitry 53 (see FIG. 5A).

The system 10 may further include a camera to capture images of the area. The camera may be configured to take individual pictures of the area at predetermined intervals, or may take video of the area either on a continuous basis or periodic basis.

The processing circuitry 51 may perform the following functions: (a) track people within a network of germicidal radiation emitters and use a computerized system of determining the location of that person; and then (b) combined with the input of the user (for example one of the four different operational modes could be chosen) and in some instances additional sensing devices, (c) adjust the output of the emitters to keep people in the environment free of harm from germicidal radiation, which, in some or most instances are being intentionally irradiated as they move about in the environment. The hoped for benefits of using smart technology to track individuals in an environment is to enable persons to be kept safe while allowing the germicidal radiation to be emitted and therefore achieving more or less continuous disinfection of the environment much more frequently and to a much greater extent than any technology currently available. It is obvious why this technology is superior and urgently needed to combat infection diseases.

The system 10 can be configured with one or a network of emitters 20 in multiple rooms capable of emitting germicidal radiation throughout the entire area. This includes the entire area, and not just limited spaces such as floors, ceilings, doorways, ductwork or enclosed air circulation devices, and usually not just in a single room (such as an operating room). The germicidal radiation is emitted throughout the area and in most operational modes is intended to treat the clothing, protective equipment, objects being carried such as pad and paper, medical apparatus such as stethoscopes, etc. of the people in the area.

The processing circuitry 51 is optionally configured to track one or more persons within the environment. The processing circuitry 51 is also configured to control the network of emitters 20 and output of the emitters 20 based on user and sensor inputs, such as detecting whether the eyes and skin are protected for the persons in this network. The system is configured to intentionally and safely expose persons in the environment to germicidal radiation. This provides for direct decontamination of the bodies of the people themselves, which can be the sources of the infection or infectious diseases. No other technology in the art provides this much needed benefit.

Figure 6:
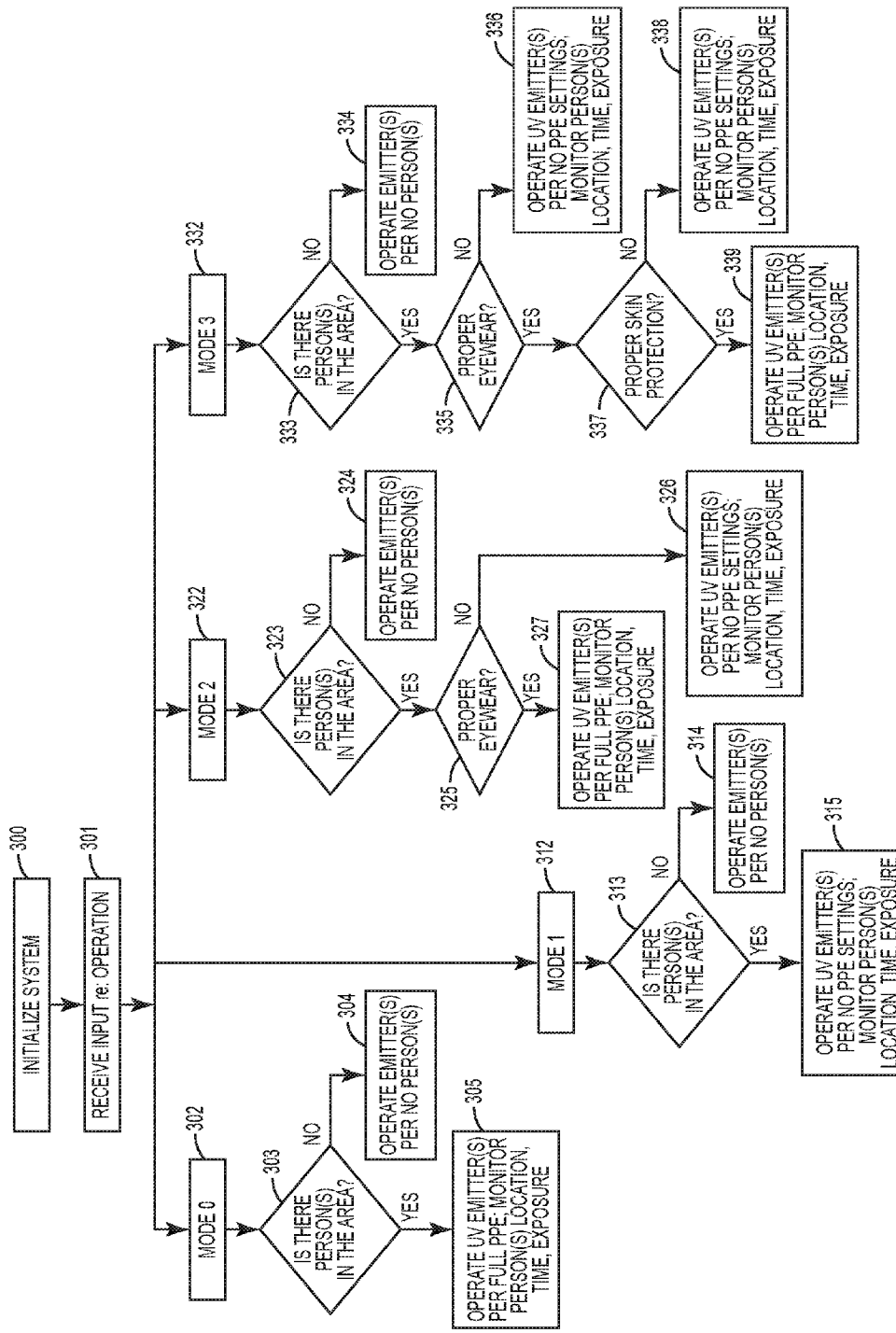
FIG. 6 is a flowchart diagram of a method of sanitizing an environment using germicidal radiation.

FIG. 6 illustrates one process of system operation to disinfect an environment 100. Prior to operation, the system 10 is initialized (block 300). The computing device 10 may perform an initial assessment of the various components of the system 10. This may include communicating with each of the various components (e.g., sensors 30, 40, emitters 20) to ensure each is in proper operational condition. In the event that a component is found to be non-operational, the processing circuitry 51 may prevent activation of the emitters 20 throughout the environment 100. Once the component becomes operational, the processing circuitry 51 may allow activation of the emitters 20. The processing circuitry 51 may also prevent initialization of just the section 110 that is directly affected by the non-operational component. Other sections 110 in which components are operational may be activated. Using the environment 100 of FIG. 2 as an example, when the processing circuitry 51 determines that a sensor 30 within room 110a is not operating properly, the processing circuitry 51 may prevent activation of the corresponding emitter 20 in that room 110a. If the other components in the environment 100 are determined to be operational, the computing device 50 may initialize the system 10 in these areas 110b, 110c, 110d.

The processing circuitry 51 then determines the operational mode (block 301). This may include an input received from the user, such as through an input device 59. The processing circuitry 51 may also be set to a default operational mode which is used unless an alternate operational mode is determined.

The processing circuitry 51 may be configured to operate in one of four different operational modes. The operational modes include different germicidal radiation emissions control schemes based on whether eye and/or skin protective equipment sensors are provided: if yes, then either Operational Modes 2 or 3 would be chosen, and if no, when protective equipment sensors are not provided, then either Operational Mode 0 or 1 is chosen depending upon whether or not protective equipment is assumed to be worn by the persons in the environment. These different Operational Modes can either be selected as an input from the user, or the processing circuitry 51 can be provided and installed pre-programmed to operate in fewer than four or even only one of the modes as a safe guard to prevent the inadvertent operation in an undesired or unsafe mode.

| Operational Mode | Persons in Area | Eye Protection | Skin Protection |
| --- | --- | --- | --- |
| Operational Mode 0 | Monitored electronically with feedback into system | Assumed Adequate, administratively controlled | Assumed Adequate, administratively controlled |
| Operational Mode 1 | Monitored electronically with feedback into system | Assumed Inadequate | Assumed Inadequate |
| Operational Mode 2 | Monitored electronically with feedback into system | Monitored electronically with feedback into system | Assumed Adequate, administratively controlled |
| Operational Mode 3 | Monitored electronically with feedback into system | Monitored electronically with feedback into system | Monitored electronically with feedback into system |

Operational Mode 0 (block 302) operates under the assumption that all persons in the area are protected from germicidal radiation exposure (protected=adequate eye and skin protection administratively controlled). In Operational Mode 0, the emitters 20 are on to decontaminate the environment. The processing circuitry 51 determines if there are any persons in the area (block 303). If there are no persons, the processing circuitry 51 operates the emitters 20 at prescribed settings (block 304) suited for no persons in the area. This mode of operation with no persons present may provide for more intense germicidal radiation exposure for more thorough decontamination or less germicidal radiation exposure to save energy costs, or a combination of more intense radiation for a period of time followed by less intense exposure to save costs. The emitters 20 may be operated continuously, or may be pulsed with periods of high radiation emission followed by periods of low or no radiation emission. The desired emission durations and frequencies will vary depending on the environment being decontaminated, the organisms being treated, and user preferences.

If there is a person in the area (block 303), the emitters 20 emit germicidal radiation per prescribed settings for persons wearing full PPE (block 305). The processing circuitry 51 tracks the location of the one or more persons, and monitors their time in the germicidal radiation environment.

Operational Mode 0 may be useful for performing testing regarding the spread of contagious diseases and the effectiveness of germicidal radiation to control those diseases. This scenario may also be useful in an operating room or intensive care unit of a hospital. The processing circuitry 51 could collect data regarding the time that each individual was in the germicidal radiation exposure and where they were within the environment; swabs could be taken, and statistically designed studies conducted to greatly enhance our understanding of how these diseases are spread and how effective continuous or semi-continuous germicidal radiation actually would be in disinfecting occupied areas.

In Operational Mode 0, persons in an area where germicidal radiation is being emitted are tracked and are assumed by administrative controls to have adequate eye and skin protection.

Operational Mode 1 (block 312) operates under the assumption that one or more persons in the area are not protected from germicidal radiation exposure. If the processing circuitry 51 determines that there are no persons in the area (block 313), the emitters 20 operate at prescribed settings for no persons in the area (block 314) as described above. If there are one or more persons (block 313), the locations of the persons are tracked and the time and germicidal radiation exposure for each person are monitored (block 315). In this mode, germicidal radiation is emitted below threshold limit values or not emitted at all where persons are present. In unoccupied sections of the area, germicidal radiation is emitted at the prescribed settings. This mode may use motion detectors or door position detectors to sense if the area is closed off from other areas containing persons, etc.

Operational Mode 2 (block 322) includes monitoring for eye protection for persons in the environment, and skin protection is administratively controlled and assumed to be adequate (either by application of germicidal radiation screen creams or full coverage of skin with clothing or PPE). If there are no persons in the area (block 323), the emitters 20 operate per prescribed settings (block 324) as described above. If it is determined that there is one or more persons in the area (block 323), the processing circuitry 51 determines whether they are wearing eye protection (block 325). If the person does not have eye protection, the locations of the persons are tracked and the time and germicidal radiation exposure for each person are monitored (block 326). In this situation the emitters 20 may also shut down immediately or after a delay and warning, such as a voice that requests person in the area to check their eye protection and make certain it is properly worn, or cut back to threshold limit value levels (block 326). If the persons have eye protection, as determined by smart PPE and PPE sensors described in detail in this application, the emitters 20 emit germicidal radiation per prescribed settings (block 327).

Methods for protecting the eyes of people in an environment of germicidal radiation may employ various forms of protection not currently available. For example, small, unobtrusive switches or sensors located in the eyewear nose pieces, bridge, frame, strap, etc., could detect whether or not the eyewear is properly fitted on the head. For example, in the case of germicidal radiation protective glasses, small switches or pressure sensors could be mounted in the nose piece and behind the head in an elastic strap. When the eyewear is in position and held in place with tension on the strap, both front and rear switches or sensors detect pressure, and these in turn communicate through a wireless transmitter (or a physical wire for persons that are relatively immobile) in the eyewear to the processing circuitry 51 indicating proper donning of the protective eyewear. Similarly, pressure sensors may be included on a strap used to secure the protective equipment to the person. If the pressure sensed is below a predetermined amount, the processing circuitry 51 interprets that the equipment is not being worn properly.

In addition to switches or sensors to detect proper donning of the eye protection, germicidal radiation protective goggles, glasses, or face shields could be enhanced with germicidal radiation blocking fabrics and materials to also protect the skin of the head and neck areas. Examples are illustrated in FIGS. 6A and 6B. A germicidal radiation barrier material could be added around the edges of the germicidal radiation protective area of the eyewear to cover the head above and face below the eyewear. This protective fabric can extend all the way around the back of the head, being attached to the strap or support that holds the eyewear in place on the head, so that both the upper head and lower head, face, and neck areas are protected from germicidal radiation. Fabrics particularly suited for blocking germicidal radiation, such as ePTFE and certified germicidal radiation protective fabrics such as those available on the website www.coolibar.com could also be utilized in this manner.

In one envisioned embodiment of Operational Mode 2, every person within the hospital environment, including patients, health care workers, and all visitors, are required to have long sleeved garments, pants that cover the entire leg, and socks and shoes that cover the feet and ankles. Each person entering the area is assigned protective headgear that has germicidal radiation protective glasses (or goggles or face shield, etc.) and a breathable germicidal radiation barrier fabric attached to the circumference of the glasses and drapes back over the head and extends from the glasses down over the face and neck area with the result that the entire head, face, and neck of the person is protected. Each person is then required to wear at all times while in the environment disposable plastic gloves with the glove material designed to block germicidal radiation. Sensors in the protective headgear are able to detect whether or not the gear has been properly donned, and a signal is sent to the control unit indicating proper donning of the headgear. The wearing of gloves and proper clothing is administratively controlled. The headgear transmits a signal to the control unit that enables the control unit to know where within the environment the headgear is located and whether or not it is properly donned. If a person in the environment were to remove their headgear, the control unit would shut off or turn down to safe levels any germicidal radiation emitters in the area of the environment where that person would be able to be exposed to radiation. A signal is then sent to a central control panel alerting personnel that there is a person in the area that is not wearing proper protection so that the situation can be addressed. In this embodiment, once the headgear leaves the environment, which will send a signal to the control circuit indicating that the headgear has left the environment, it is assumed that the person also has left the environment, and thus a separate person tracking system is not required. A more robust version of this Operational Mode 2 embodiment would include the system described in this paragraph but also would include a separate person tracking system, such as flexible RFID bracelets given to everyone entering the environment in addition to assigning the headgear, so that the control unit independently tracks both the location of the headgear and each person in the germicidal radiation emitting environment.

In Operational Mode 3 (block 332), the processing circuitry 51 determines whether there are any persons in the environment. If there are no persons in the area (block 333), the emitters 20 operate at prescribed settings (block 334) as described above. If there are persons, eye and skin protection is monitored for everyone in the environment (block 335). If there is no adequate eye protection, the emitters 20 may shut down immediately or after a delay and warning, or cut back to threshold limit value levels (block 336).

If there is proper eye protection, the processing circuitry 51 detects for skin protection (block 337). If there is no adequate skin protection, the emitters 20 may shut down immediately or after a delay and warning, or cut back to threshold limit value levels (block 338). If there is proper skin protection, the emitters 20 emit germicidal radiation per prescribed settings (block 339). In this third mode, if the protective eyewear comes off or the cameras with computer analysis detect skin that is not adequately protected, the germicidal radiation emitters 20 are cut back accordingly to a safe level. In another embodiment of Operational Mode 3, eye protection sensors are not provided and are assumed to be adequate and controlled administratively, and only skin protection monitoring is provided. In yet another embodiment of Operational Mode 3, video monitoring and computer analysis of the images determines whether both eye and skin protection are properly donned to protect the individuals from germicidal radiation exposure.

Figure 7:
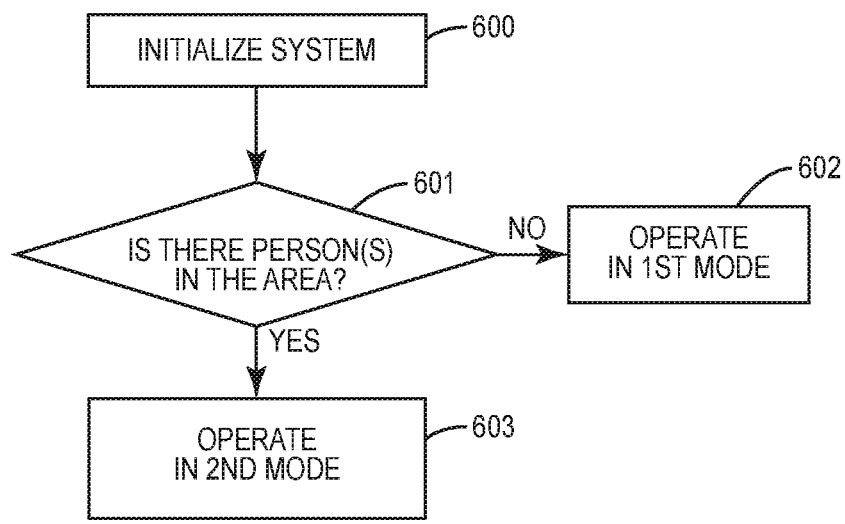
FIG. 7 is a flowchart diagram of a method of sanitizing an environment using germicidal radiation.

FIG. 7 illustrates one process of system operation to disinfect an environment 100. Prior to operation, the system 10 is initialized (block 600). The processing circuitry 51 may perform an initial assessment of the various components of the system 10. This may include communicating with each of the various components (e.g., sensors 30, 40, emitters 20) to ensure each is in proper operational condition. In the event that a component is found to be non-operational, the processing circuitry 51 may prevent activation of the emitters 20 throughout the environment 100. Once the component becomes operational, the computing device 51 may allow activation of the emitters 20. The processing circuitry 51 may also prevent initialization of just the section 110 that is directly affected by the non-operational component. Other sections 110 in which components are operational may be activated. Using the environment of FIG. 2 as an example, when the processing circuitry 51 determines that a sensor 30 within room 110*a* is not operating properly, the processing circuitry 51 may prevent activation of the corresponding emitter 20 in that room 110*a*. If the other components in the environment 100 are determined to be operational, the processing circuitry 51 may initialize the system 10 in these areas 110*b*, 110*c*, 110*d*.

After initialization, the processing circuitry 51 then determines if there is a person in the environment 100 (block 601). This may include receiving signals from the sensor(s) 30 in the environment 100 indicating the presence of a person. As stated above, the sensor(s) 30 may use a variety of different technologies to detect a person, such as movement sensors, heat sensors, sound sensors, and even the presence of smart eye protection in the environment can be a surrogate indication of the presence of a person, when each person in the area is assigned a specific unit of smart eye protection.

Detecting a person in the environment 100 may also occur when the person first enters. The processing circuitry 51 may require that the person pass through a particular location which is equipped with a sensor 30 to detect the person. In one embodiment, entrances into the environment 100 are kept locked and require user input through an input device 59 prior to admission. This may include a user swiping an ID card through a card reader, or entering a code into an input device 59. FIG. 1 includes this concept with a card reader 59 positioned at the door of the environment 100. This user input may be passive, such as the user walking within proximity of a sensor 30, or the person being given an RFID or like device that is read to signal entry.

In one embodiment, initial input of entry by a person provides the processing circuitry 51 with the number of persons in the environment 100. The processing circuitry 51 then tracks the location of the person as they move within the environment 100. In the event that the processing circuitry 51 loses the person's location, the emitters 20 throughout the system 10 may be deactivated to prevent inadvertent ultraviolet radiation exposure to the person. Once the location of the person is detected, or the person is otherwise accounted for as having left the environment 100, the system 10 may again be activated. To facilitate tracking, persons in the environment 100 may be required to exit through one or more particular exits that are equipped to detect the person leaving the environment 100. These exits may include similar technology as described above for the entrance.

If the processing circuitry 51 determines that there is a person in the environment 100 (block 601), the processing circuitry 51 operates in second mode (block 603). As explained in more detail below, this may include emitting different amounts of germicidal radiation, or emitting the radiation in different manners (e.g., different exposure amounts, different peak emissions).

In one embodiment, the system 10 operates the same throughout the entire environment 100. When no persons are detected in the environment 100, the emitters 20 operate at the first mode. Once the processing circuitry 51 detects that a person is in the environment 100, the emitters 20 operate in the second mode throughout the entire environment 100. Using FIG. 2 as an example, the emitters 20 throughout the entire environment 100 including the different rooms 110*a*, 110*b*, 110*c*, 110*d* operate in the first mode when no persons are in the environment 100. Once the processing circuitry 51 detects a person anywhere in the environment 100, the emitters 20 throughout the entire environment 100 including the different rooms 110*a*, 110*b*, 110*c*, 110*d* operate in the second mode. This occurs regardless of whether the person is in a particular room 110 (i.e., emitters in room 110*b* operate at the second mode despite the person being located in room 110*a*).

The system 10 may also be configured to divide the environment 100 into multiple sections 110. The processing circuitry 51 is able to determine the section 110 where the person is located and operate in different modes in the different sections 110. The processing circuitry 51 operates in the first mode in the sections 110 away from the person, and in the second mode in the section 110 where the person is located.

One embodiment can be described using the example of FIG. 2. The environment 100 includes the different rooms 110*a*, 110*b*, 110*c*, 110*d*. The location of the person is tracked through each section 110 in the environment 100. When the person is located in a particular section, the processing circuitry 51 operates in the second mode in that section 110 and in the first mode in the other sections 110. For example, if the person is determined to be in section 110*c*, the emitters 20 in that section 110*c* operate in the second mode. The emitters 20 in the other sections 110*a*, 110*b*, 110*d* operate in the first mode. When the person moves into another section 110, the processing circuitry 51 changes the modes accordingly. For example, when the person moves from section 110*c* to section 110*a*, the emitters in section 110*a* are changed to operate in the second mode. The emitters in section 110*c*, along with those in sections 110*b* and 110*d* operate in the first mode.

The system 10 may be further configured with door sensors to monitor the doors that separate the different sections 110. In the event a door is open between the different sections 110, the system may treat both sections 110 together and operate their respective emitters 20 in a like manner. For example using FIG. 2, if a person moves from section 110b into section 110a, the emitter 20 in section 110b may thereafter operate in the first mode. However, if the door that separates the sections 110b, 110a remains open, the processing circuitry 51 may continue to operate the emitters 20 in the section 110b in the second mode (along with section 110a where the person is now located).

Figure 8:
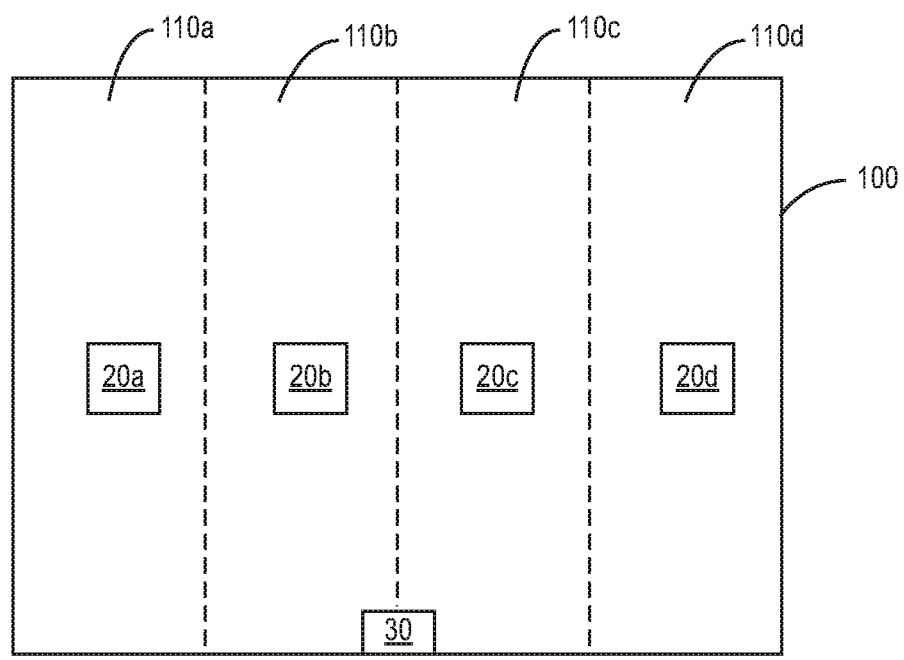
FIG. 8 is a schematic diagram of a single room environment that is divided into multiple sections.

The system 10 may also be configured to divide rooms into separate sections 110. FIG. 8 includes a single room environment 100 that is divided into multiple sections 110. Specifically, the room 100 is divided into four sections 110a-110d. Each section 110 includes a separate emitter 20 that operates independently of the others. Each emitter 20 is further configured to emit germicidal radiation just within their respective section 110. When a person is in a particular section 110, the corresponding emitter 20 operates at the second mode while the emitters 20 in the other sections 110 operate at the first mode. If the person were to move into a different section 110 in the room 100, the emitter 20 in that new section 110 changes to the second mode while the section 110 form which the person moved changes to the first mode. In FIG. 8, each of the sections 110 is the same size, however, the sections 110 may include different relative shapes and/or sizes.

Figure 9A:
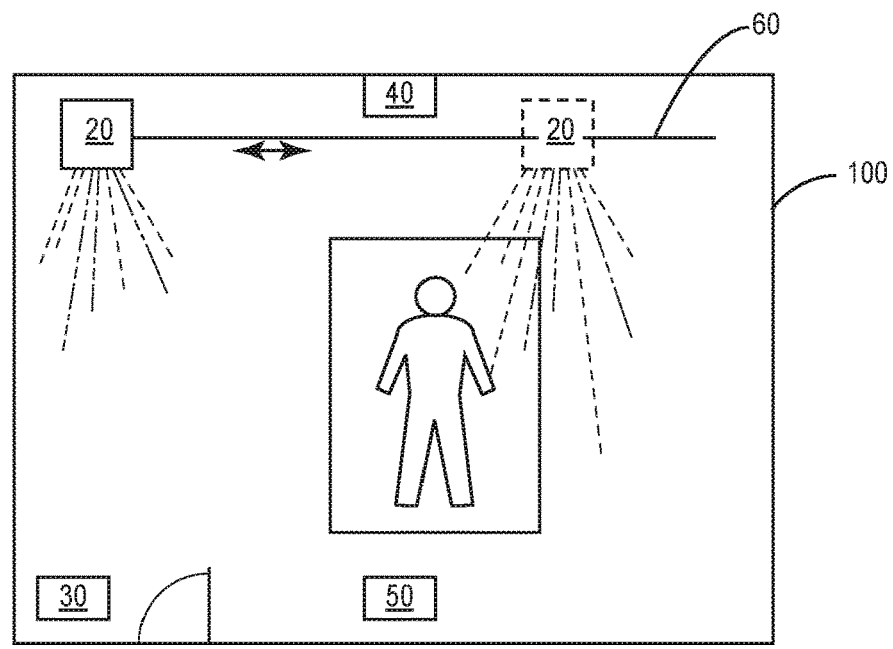
FIG. 9A is a schematic diagram of a system with a movable emitter.

In another embodiment, the emitter 20 is able to physically move to different locations within the environment 100. The physical movement is automated and can be accomplished by the emitter being mounted on a movement device 60 that creates physical movement of the emitter 20 within the environment 100. The movement device 60 that creates physical movement can be a motorized track or a pole to move the emitter 20 back and forth in a linear movement, as shown in FIG. 9A, the advantage being that the environment 100 is decontaminated from more than one vantage point and more surfaces can be decontaminated quickly and easily. This "moving source" configuration overcomes a major problem with germicidal radiation decontamination techniques, that is that they decontaminate primarily in "line of sight" of the radiation; nooks and crevices and shadow areas are significantly less impacted unless the radiation is reflected off of surfaces and manages to get into the cracks.

Figure 9B:
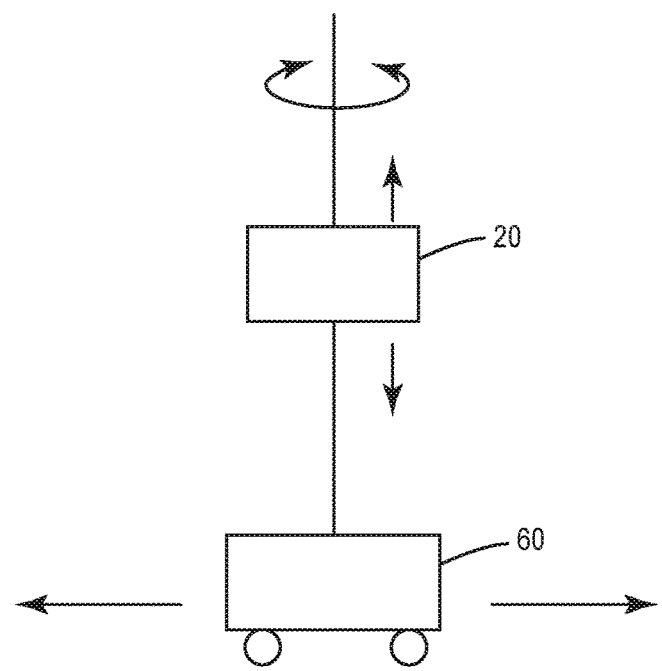
FIG. 9B is a schematic diagram of a device that moves the emitter in the environment.

Any electromechanical means of creating physical movement of the emitter 20 can be considered for the movement device 60, including mounting the emitter 20 on a robotic vehicle or other device that is free to move throughout the room 100 as shown in FIG. 9B. Any combinations of one, two, or three dimensional movement or rotational movement achieved by any mechanical or electromechanical means known are possible embodiments. In FIG. 9B, the movement device 60 is propelled by motorized wheels to move to different locations in the environment, and the emitter 20 mounted on the vertical pole allows for 360 degree rotation as well as vertical movement up and down, allowing this one device to move the emitter to enough different locations, elevations, and angles within the environment to effect thorough decontamination of areas that might be missed in cases where the emitter 20 is in a fixed location in the environment. In such an instance, the floor plan could be programmed into the movement device 60, or the movement device could have sensors that allow it to determine where in the room the obstacles are and move around these when possible, technology similar to that employed in robotic floor cleaners commercially available today. In these embodiments with moving germicidal radiation sources, the primary features described in earlier embodiments are preserved, namely the ability to detect whether persons in the environment have eye protection properly donned and the ability to control the sources 20 in the event of detecting persons in the environment who are not protected, thereby keeping persons in the environment safe from unsafe levels of germicidal radiation exposure. The feature of moving emitters does not change in any way the basic functioning of the protective features of this invention.

In the various embodiments, once the processing circuitry 51 detects a person is in the environment, the device 50 may then detect whether the person has protective equipment. Equipment that shields a person, such as a tent or protective screens, may be equipped with switches and sensors and the like that detect whether it is in use. When the equipment is in the proper location on the person, the switch or sensors are in a "satisfied" position, indicating proper use. When the equipment is improperly positioned or not in use, the switch or sensors are not indicating proper use and remain in an unsatisfied position. The processing circuitry 51 receives signals from the switches and sensors to determine the proper use of the equipment. Germicidal radiation sensors can also be provided under this tent like structure to ensure that the person inside is not being exposed to harmful germicidal radiation.

A vision sensor (e.g. a video monitoring system) 40 may also be located in the environment to capture the location of the protective equipment. If it is determined that the protective equipment is in the correct position, the processing circuitry 51 accepts that the equipment is in proper use. Facial recognition computer algorithms could be used to determine whether or not the protective equipment, especially the eye protection, is being worn properly.

Equipment that is worn by the person (e.g., eye protection, clothing, headwear) may be detected in a different manner. Each person that enters the environment may be equipped with a communication unit, and the protective equipment is equipped with an identifier as explained above. The communication unit periodically polls for the existence of the identifiers. If the unit does not receive a signal from the identifier, the unit communicates with the processing circuitry 51 thus indicating that the protective equipment is not being worn.

The control signal from the processing circuitry 51 to the germicidal emitter 20 can be conveyed by hard wiring or conveyed wirelessly. Wireless control signals have several benefits. First, the installation costs should be significantly lower than hard wiring; second, temporary systems can be installed and removed without making any holes in walls and ceilings, etc. One very simple system envisioned has a centrally located computing device 50 powered by a local 110V duplex receptacle, perhaps at a nurse's station. Each emitter, perhaps single or multiple light sources that are freestanding in a corner or wall hanging designs that plug into a nearby 110V receptacle, communicates wirelessly with the computing device 50, as do all of the protective eyewear devices worn by persons in the area or skin monitoring systems in the area. Third, a wireless control signal to the germicidal emitter enables the use of the moving robotic emitter 20, which could be roaming the hallways or decontaminating under the beds or other hard to get to locations. Fourth, wireless control signals allows the emitter to be moved as needed to optimize decontamination or just temporarily moved out of the way without creating additional costly wiring changes.

Sensors 40 may also be configured to detect for exposed skin on the person. Sensors 40 may include an infrared or similar camera monitor or sensor that detects the temperature of any exposed skin. Based on this input, the processing circuitry 51 is able to detect whether the person is wearing clothing and/or lotion. The protective equipment results in a lower temperature reading which can be signaled to the processing circuitry 51 indicating the existence of the proper protective equipment.

Sensors 40 may also capture skin color. Lotions that are to be applied to the skin of the person may be colored which is captured by the monitor or sensor 40. For example, the lotion may include white or brightly colored pigments that provide a high visual indication when worn by the person. The lotion may also include a fluorescent marker or dye that causes the skin to have a different visual appearance when viewed by the camera 40. In one embodiment, these materials cause the skin to "glow" when exposed to ultraviolet light. The sensors 40 capture the skin color and the system is able to detect and differentiate bare skin (i.e., unprotected skin) from that with protection (e.g., lotion, clothing).

In another embodiment, camera monitors are employed that are able to detect human skin. A combination of video monitoring and analysis methods could be used, one that detects skin that has no protective clothing covering it, and another system that analyzes whether or not the skin has a coating of germicidal radiation protective substances, as indicated by a dye or colorant in the protective substance that is able to be detected by the monitoring system and analyzed by the computer. There are a variety of fluorescent dyes and colorants that could be used, and the skin protective coatings could be creams, lotions, and even film forming polymeric coatings. A further embodiment is a cream, lotion, or film forming skin coating that is a combination of (a) germicidal radiation protective ingredients, (b) dyes and colorants and other additives that are able to be readily detected by monitoring systems, especially those that are transparent to the human eye but which show up readily when viewed with different wavelengths of light such as UV light, and (c) germicidal additives that assist in the destruction of microbes.

The skin cream applied to a person may have germicidal activity from either the use of organic chemicals added to the cream or the use of nanoparticles of TiO2 or other particles that have germicidal activity in the presence of germicidal radiation. Nano sized TiO2 particles have a catalytic effect to destroy microbes when light hits the particles.

In one embodiment, the processing circuitry 51 determines in a binary manner whether the person has protective equipment. If the person has protection, the processing circuitry 51 operates in a particular manner. If the person does not have protection, the processing circuitry 51 operates in a different manner. The processing circuitry 51 may also be configured to determine intermediate degrees of protection. For example, the processing circuitry 51 may be able to detect an amount of lotion that is applied on the skin based on the detected temperature and/or skin coloring. The processing circuitry 51 may then operate in intermediate modes.

In one embodiment, the system 10 includes one or more heat sensing cameras to detect if there are areas of a patient's skin, when they are exposed to germicidal radiation, are getting warmer than the surrounding areas. The elevated temperature may indicate that the skin is not protected adequately. Upon the detection of the elevated temperature, the processing circuitry 51 can either stop the emitters 20 or reduce the amount of germicidal radiation. The processing circuitry 51 may also be configured to cause a signal to be sent to a remote party (e.g., nurse) who can then more closely evaluate the situation.

Figure 10:
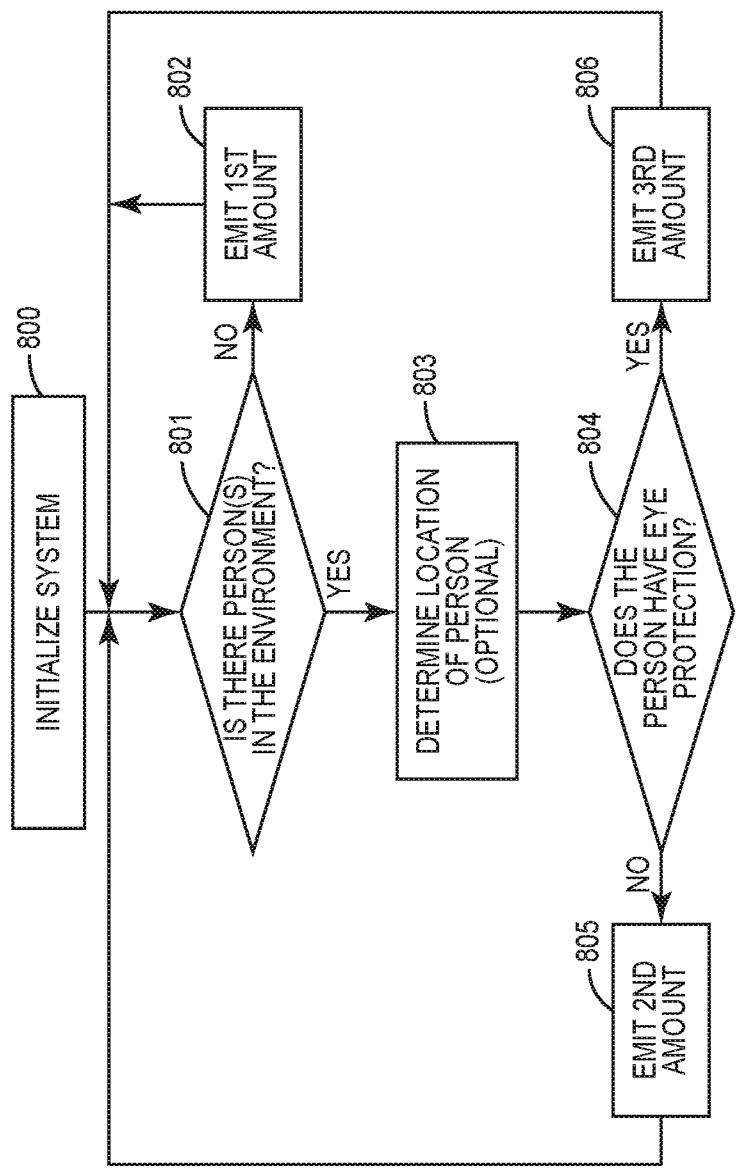
FIG. 10 is a flowchart diagram of a method of sanitizing an environment using germicidal radiation.

FIG. 10 illustrates a method of sanitizing an environment 100 using germicidal radiation. The method includes initializing the system 10 and ensuring the various components are in proper operating condition (block 800). Once the system 10 is initialized, the processing circuitry 51 determines whether a person is in the environment 100 (block 801). If no person is detected, the system emits a first amount of germicidal radiation (block 802). If a person is detected (block 801), the processing circuitry 51 then optionally determines the location of the person (block 803). The processing circuitry 51 also determines whether the person has eye protection (block 804). If there is no eye protection, a second amount of germicidal radiation is emitted (block 805). This may include emitting no germicidal radiation. If eye protection is being used (block 804), a third amount of germicidal radiation is emitted (block 806). The third amount may be between the first and second amounts, or may be the same as the first amount.

The various embodiments may include detecting a single person in the environment, or multiple people in the environment 100. This may include emitting a first amount of ultraviolet radiation in the one or more sections 110 that do not include any person, and emitting a second lesser amount in the one or more sections 110 that do include one or more persons. The processing circuitry 51 may also be configured to increase the amount of germicidal radiation emitted when the number of persons in the environment increases. This is advantageous because the decontamination load increases when more persons are present, plus it is known that microbes settle out on surfaces; thus walking and movement increases air currents and the chances that microbes become airborne once again, thereby increasing the chances of spreading infection.

The processing circuitry 51 may also be configured to adjust the germicidal radiation emissions and or the modes of operation through auditory signals. The system 10 includes one or more noise sensors in the environment that is able to detect noises and speech. The processing circuitry 51 is configured to change the emission based on this detected information. In one embodiment, the processing circuitry 51 is configured to receive voice commands to adjust the settings. For example, the voice command "germicidal radiation off" may cause the emitters 20 in the section to deactivate. Similar commands may include but are not limited to "germicidal radiation on", "lower germicidal radiation", and "pause germicidal radiation". Other noises may also cause a change in emissions. For example, detecting a cough or sneeze from a person in the area may increase the amount of germicidal radiation emitted for a predetermined period of time.

The skin protection may include the use of a "head tent" by a patient in an environment with germicidal radiation exposure shown in FIG. 3. This tent includes a small frame with germicidal radiation and/or light blocking materials covering the frame. The tent is sized to extend over the user's head when they are in bed such that the person can sleep easily in an environment of germicidal radiation exposure (this assumes the rest of his or her body is covered by sheets or blankets) without having to wear glasses or worry about face and neck skin coverage. But at the same time, the environment around the bed is continuously being decontaminated while sleeping. The system can be set up to detect sleeping patients and even intensify germicidal radiation for a deeper purification during those times.

The processing circuitry 51 may identify and/or monitor persons in the area by wrist or ankle bands, lanyards, or any other means to attach a transmitting or other location detecting device to a person. Location monitoring may also be achieved by assigning personal protective equipment (PPE) to persons entering the area wherein a locating device is embedded in the PPE. For example a location detection transmitter could be installed in a pair of germicidal radiation safety glasses or other eye protecting device, or a location detection transmitter could be installed in an obscure part of a germicidal radiation protecting overgarment, such as a smock or light coveralls. Also, combinations of systems could be used. For example, a tracking system could be used with small transmitters attached to PPE or wristbands, etc. as described above, plus a video monitoring system could be used to identify separate persons. This could be used as a back-up to ensure that persons in the area have been accounted for. By monitoring where in the germicidal radiation exposure areas each person is at all times, the processing circuitry 51 can provide greater assurance that persons in the environment are not exposed to harmful levels of germicidal radiation.

In one application in a patient's room, the patient wears a smart wrist band. One or more sensors 30 are configured to determine where the person is in the room or otherwise in the environment 100. If the person is determined to not be in the bathroom, for example, and the bathroom door is closed, then the bathroom germicidal radiation emitters 20 are turned on and to the desired level automatically. If the patient does enter the bathroom, then the germicidal radiation emitters 20 in this area could either be turned off or turned down to threshold limit value levels such that it would be safe to remove the protective eye wear and skin cream (such as in a shower) and not be over exposed to germicidal radiation. The processing circuitry 51 could be set to expose the main bed area to germicidal radiation or more intense germicidal radiation whenever the patient enters the bathroom, provided there are no unprotected persons in the main bed area when the patient enters the bathroom.

Another example may be during times of low activity (night or other times) in a hallway or closet area. The processing circuitry 51 monitors the locations of persons in the environment and adjusts germicidal radiation levels accordingly.

The assigning of identification could be done administratively. Procedures could be put into place requiring persons entering into the environment to have the location monitoring device on. The system 10 may also include a person detection video monitoring system that automatically detects whether or not someone is in the germicidal radiation area without the location monitoring device on their person.

The location identification system could also be built in to the protective eye protection, so that everyone when entering this room or ward is assigned eye protection that is not to be removed except in designated areas (like bathrooms). The eye protection not only serves the function of determining whether the eyes are protected but also identifies for the processing circuitry 51 the existence of a person in the area and where the person is in the area.

PPE eyewear may include a variety of different configurations, such as goggles, faceshields, glasses, full helmet, night shades, smart video head gear with monitor (similar to gaming gear worn on head and face but this could project to the patient any video, online content, TV, etc.), a "tent" for the head for sleeping, and any number of other specialized smart head protection devices whose primary function is to protect the eyes from germicidal radiation but which simultaneously may also protect the skin of the head and neck and upper body and may also serve other functions. The primary smart function desired is the continuous monitoring of whether or not the head gear is properly donned and thus by implication protecting the patient's eyes from germicidal radiation.

This eye protection would be for use for patients, health care workers (HCW's), visitors, and anyone else in the area of germicidal radiation exposure.

Pressure sensors could be mounted around a head band (like a hard hat type hear strap) that would sense pressure against the head. Once the sensors detect a certain amount of pressure in certain areas, the PPE is equipped with a wireless transmitter to send a wireless signal to the controller that allows the germicidal radiation emitter to turn on. If the pressure sensors detect loss of pressure (in the event the headpiece comes off, for example), then a wireless signal is sent which would cause the processing circuitry 51 to deactivate the germicidal radiation emitters 20. In the case of eyeglasses, pressure sensors could be located in the nose pads of the glasses and optionally on the ear pieces to sense when the glasses are properly positioned on the face. Or, an elastic band could be used to hold the glasses onto the face, and pressure could be sensed from a pressure sensor placed on the inside of the elastic that senses pressure against the head. If the pressure sensor at the back of the head and the pressure sensors at the nose pad detect pressure, then the glasses can be assumed to be worn properly. Goggles can be done the same way.

Temperature sensors, touch sensors, humidity sensors, etc., may also be useful to determine whether or not the PPE is being worn correctly. For example, a temperature sensor in the nose pad or other location would indicate that it is being worn against the skin, and a humidity sensor may pick up humidity from the skin. Also, heartbeat and body temperature monitoring and other physiological monitoring of the patient could also be added to the PPE monitoring system as an added benefit.

A current sensor (contact with skin completes microcurrent circuit and indicates the PPE is on), proximity sensors, infrared sensors, ambient light sensors (or lack thereof if the nose piece is against the nose), position sensors, color sensors, any of these and many other sensors could also be useful in determining whether or not PPE has been donned properly.

Skin protection may also be performed in various manners. One manner includes skin monitoring such as through video analysis to determine whether (a) there is exposed skin (in cases where skin creams are not used) or (b) there is exposed skin not adequately protected by germicidal radiation screening creams or lotions. Various means could be employed to determine adequate coverage. One way is to include lotions that are colored (white pigments could be used to both provide better germicidal radiation protection as well as a highly visual indication that the cream has been applied to the skin. Video monitors in the room where germicidal radiation exposure is present monitor the persons and are able to detect and differentiate bare skin from clothing or gloves or other protection. The computer then determines whether or not there are areas of skin that do not have adequate cream applied. If not, the germicidal radiation system is shut down or reduced and an alarm is sounded.

Another manner is to include a fluorescent marker or other dye that causes the skin when analyzed to "glow". A germicidal radiation blocking cream, lotion, or coating may include a fluorescent marker, along with an optional germicidal substance to kill bacteria. In one embodiment, prior to activating the germicidal radiation emitters 20, the patient or nurse could spread the cream on exposed skin areas, then turn on a blacklight to visually ensure that the skin areas are coated turn based on the bright appearance of the fluorescent marker in the coating. This would facilitate inspection to determine if any areas were missed. Once the coating is checked and confirmed to be adequate, the system is armed, and the germicidal radiation emitters 20 can be activated. A variety of basic colors and combinations are used that fluoresce under UVA light and have some color under normal light (although not as brilliant under normal light). These colorants could be added to the lotion to check for adequate coverage with and without the black light. Pictures of fluorescing body paint application reveal that uncoated skin and non-fluorescing surfaces are very dark in contrast to the fluorescent painted areas.

Some colorants are "glow in the dark", that is, after exposure to normal light they glow once light has been turned off. These are effective without the need for UVA. These colorants could be added to a germicidal or non-germicidal UV blocking cream and applied to the skin. The lights could be turned off for a clear visual indication of where the cream has been applied and whether or not spots on the skin were missed.

Different colors could be used to confirm proper application. For example, a base of one colorant (fluorescing or non-fluorescing) could be applied. In one embodiment the base coat is the foundation of the colorant and does not contain colorant. The base foundation may include one of the fluorescing colorants. A topcoat cream is then applied over the foundation that contains a very different, contrasting fluorescing color. With the application of the blacklight, if any of the first color is seen, it is an indication that there is inadequate coverage. Even if there is a mixture of color between the base and the top coat, that would be an indication of inadequate coverage. Only when the topcoat color only was visible would the application be complete and ready for germicidal radiation (e.g., UV-C). In a similar embodiment, a fluorescing color added to the base but a non-fluorescing color in the top layer. When the skin is adequately covered, no fluorescing should be visible when a black light is turned on. The key to any of these embodiments is the ability to quickly recognize when the base layer against the skin is not adequately covered. The two layer system is designed to make the layer against the skin which is not adequately protected from germicidal radiation exposures more visible.

The various lotion applications may use both coalescing polymer films (latices) as well as non-coalescing coatings such as creams or lotions. In the case of the latex polymer films, the formulation includes pigments and additives to block germicidal radiation and optionally provide germicidal benefits. An advantage of a latex film would be a protective layer that is more durable and does not rub off as easily as the patient moves about. If polymers are chosen that inherently block UV light, a thin polymer skin layer may adequately protect persons in the environment and have a variety of advantages.

If needed to enhance video analysis to detect bare skin, a substance could be applied to the bare skin, such as after showering, that dries and contains a residue of some innocuous substance that is harmless to the person but which stands out prominently when viewed by the video monitoring system. Applied creams or garments would cover this substance, thus confirming to the system that there is not bare skin. If the skin then becomes exposed, either by the clothing being removed or the germicidal radiation protective cream wiping off, the monitor detects the exposed skin and shuts down the germicidal radiation system.

In one embodiment, visitors to the area would have a face shield with a light fabric that covers the hair and skin. Persons are required to wear long sleeves, pants, and gloves, therefore exposing no skin in the germicidal radiation area. Video monitors equipped with skin detection such as demonstrated in this video would be able to sound an alarm or cut back or cut off the germicidal radiation if exposed skin is detected or skin that does not have sufficient coverage with a cream or lotion or clothing.

The various skin detections can be run in tandem. For example, system A monitors exposed skin, system B monitors for fluorescence of a substance that has been added to the skin cream that fluoresces under UV light, and system C monitors the skin temperature. If exposed skin that is fully covered by fluorescing material shows a high temperature, then the system cuts off because it is assumed that in spite of precautions taken, the skin is overheating. If exposed skin is not fully covered by fluorescing material, then the system also cuts off because it is assumed that the coverage of the cream was not complete or was rubbed off. (The system would cut off in that case even if the temperature of the skin was not elevated because it is assumed that the skin is not adequately protected.)

In one embodiment, small, smart, germicidal radiation sensors and transmitters could be attached to the skin in various places (back of hand, neck, arms, etc.), and if ever these sensors detected germicidal radiation above certain levels, the system could cut back on germicidal radiation or take other appropriate action.

Infrared sensors or other sensors could monitor the temperature of any exposed skin. These are remote sensing devices that can detect warmer and cooler objects. If the IR cameras were zoomed in on the skin surface, the computer may be able to detect which areas of the skin were warmer than normal, thereby perhaps indicating an overexposure event which would trigger an action. It is possible that any damage to the skin is associated with an elevated temperature first, and thus, as long as all the exposed skin is below a certain temperature, any germicidal radiation that may be striking the skin may be assumed to be causing no harmful effects. Continuous IR monitoring of persons in germicidal radiation treatment areas can serve as a primary or backup means to ensure that no skin areas are overexposed to germicidal radiation. Thermal imaging can also be used to detect and count persons in the area.

In one embodiment, the processing circuitry 51 includes activity based controls. For example, if people enter the room such as health care workers or visitors, the processing circuitry 51 would increase the germicidal radiation to diminish the likelihood of the transfer of disease to/from the visitors. Also, increased foot traffic or movement of sheets and bedding can stimulate the aerosolization and airborne transmission of microbes. Microbes tend to settle on surfaces, and movement can stir them up. Increased motion is an indication of a need for additional germicidal radiation treatment.

The equipment worn by persons in the area may be equipped with additional features. One feature includes a display and/or LED lights that are mounted in one corner of the eye protection. This indicates to the wearer whether or not the PPE is properly worn. Another feature is an audible voice or alarm tone that can be used to communicate to the wearer or local nursing staff when the PPE is first donned properly and when it comes off. The equipment may also include a microphone to allow the person to communicate voice commands that are transmitted wirelessly by a transmitter to the processing circuitry 51. This may include control commands such as "turn off germicidal radiation", or "germicidal radiation low" or "germicidal radiation high". Other voice activated controls may also be included, such as room lighting, television activation and channel, and nurse calling. The equipment may also include one or more sensors to monitor the person, such as blood pressure, heart rate, and other data of interest. This information could then be transmitted to the processing circuitry 51.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive.

What is claimed is:

1. A system for disinfecting an environment, the system comprising:
    a germicidal radiation emitter that emits germicidal radiation into the environment to disinfect the environment;
    a sensor configured to detect whether a person in the environment is wearing eye protection on a head of the person and over eyes of the person; and
    processing circuitry communicatively coupled to the germicidal radiation emitter and the sensor, wherein the processing circuitry is configured to operate the germicidal radiation emitter to emit germicidal radiation into the environment in a first mode in response to detecting that the person is wearing the eye protection in the environment, and in a second mode in response to detecting that the person is not wearing the eye protection in the environment, with the second mode being a lower amount of germicidal radiation being emitted into the environment than the first mode;
    the second mode including either a positive amount of the germicidal radiation being emitted into the environment or no germicidal radiation being emitted into the environment.

2. The system of claim 1, wherein the germicidal radiation emitter emits at least one of UV-C, UV-B, and HINS (high intensity narrow spectrum) germicidal radiation into the environment.

3. The system of claim 1, wherein at least two of the germicidal radiation emitter, the sensor, and the processing circuitry transmit data using wireless transmissions.

4. The system of claim 1, further comprising a person sensor that senses the environment and transmits signals to the processing circuitry which is configured to determine a number of people in the environment.

5. The system of claim 1, wherein the germicidal radiation emitter is configured to move to different locations within the environment while emitting the germicidal radiation.

6. The system of claim 1, further comprising a protection sensor included with the eye protection configured to sense a position of the eye protection relative to a body of the person and to transmit signals to the processing circuitry, the processing circuitry configured to determine if the eye protection is extending over the eyes of the person prior to emitting the germicidal radiation in the first mode.

7. The system of claim 1, further comprising a germicidal radiation sensor that is mounted on an inner side of the eye protection to detect an amount of the germicidal radiation that reaches the inner side of the eye protection when the germicidal radiation is emitted, the germicidal radiation sensor being configured to transmit the detected amount to the processing circuitry.

8. The system of claim 1, wherein the sensor comprises a camera to capture images of the environment, the processing circuitry being configured to analyze the captured images to determine a number of persons in the environment and whether the persons in the environment are wearing the eye protection.

9. The system of claim 1, wherein the eye protection comprises a transparent shield configured to block the germicidal radiation while allowing at least some visible light to pass through.

10. The system of claim 9, wherein the eye protection further comprises one or more transparent sections and a material section that is attached to and extends from the transparent shield and is configured to block the germicidal radiation, the eye protection being sized such that when worn by the person the transparent shield extends over at least one of eyes, head, face, and neck of the person, and the material section extends over the head and neck of the person.

11. A method of disinfecting an environment comprising:
    determining whether a person in the environment is wearing eye protection;
    in response to determining that the person in the environment is wearing the eye protection, emitting germicidal radiation into the environment at levels to disinfect the environment and in excess of limits considered safe for humans who are not wearing eye protection; and
    in response to determining that the person in the environment is not wearing the eye protection, emitting a lesser amount of or no germicidal radiation into the environment.

12. The method of claim 11, further comprising a sensor configured to sense the environment and to transmit signals to processing circuitry that is configured to determine a number of people in the environment.

13. The method of claim 11, wherein the eye protection comprises a transparent shield capable of blocking germicidal radiation while allowing at least some visible light to pass through, the transparent shield comprising one or more transparent sections and a material section that is attached to and extends from the transparent shield and is capable of blocking the germicidal radiation, the eye protection being sized such that when worn by the person the transparent shield extends over the eyes of the person and the material section extends over the head and neck of the person.

14. The method of claim 11, further comprising a protection sensor on the eye protection configured to sense a position of the eye protection relative to a body of the person and to transmit signals to processing circuitry, the processing circuitry configured to analyze the signals to determine if the eye protection is extending over eyes of the person prior to emitting the germicidal radiation into the environment in excess of limits considered safe for humans who are not wearing the eye protection.

15. A system for disinfecting an environment, the system comprising:
- a germicidal radiation emitter that emits at least one of UV-B, UV-C, and HINS (high intensity narrow spectrum) radiation into the environment at levels in excess of limits considered safe for humans who are not wearing eye protection that extends over eyes of a person;
- a sensor configured to detect whether the person in the environment is wearing the eye protection; and
- processing circuitry communicatively coupled to the germicidal radiation emitter and the sensor;
- the processing circuitry configured to operate the germicidal radiation emitter at levels to disinfect the environment in excess of the limits considered safe for humans who are not wearing the eye protection in response to determining that the person is wearing the eye protection in the environment;
- the processing circuitry configured to operate the germicidal radiation emitter to decrease the germicidal radiation to levels considered safe for humans who are not wearing the eye protection in response to detecting that the person is not wearing the eye protection in the environment.

16. The system of claim 15, further comprising a person sensor that senses people in the environment and transmits signals to the processing circuitry which is configured to determine a number of people in the environment.

17. The system of claim 15, wherein the eye protection comprises a protection sensor configured to sense a position of the eye protection relative to a body of the person and to transmit signals to the processing circuitry, the processing circuitry configured to analyze the signals to determine if the eye protection is extending over the eyes of the person prior to emitting the germicidal radiation into the environment in excess of limits considered safe for humans who are not wearing the eye protection.

18. The system of claim 15, wherein the eye protection comprises a transparent shield configured to block the germicidal radiation while allowing at least some visible light to pass through, the transparent shield comprising one or more transparent sections and a material section that extends outward and blocks the germicidal radiation, the eye protection being sized such that when worn by the person the transparent shield extends over the eyes of the person and the material section extends over the head and neck of the person.

19. The system of claim 15, further comprising a germicidal radiation sensor that is mounted on an inner side of the eye protection and configured to measure an amount of the germicidal radiation that reaches the inner side of the eye protection when the germicidal radiation is emitted, the germicidal radiation sensor configured to transmits the measured amount to the processing circuitry.

20. The system of claim 15, wherein the sensor comprises a camera to capture images of the environment, the processing circuitry being configured to analyze the captured images to determine a number of persons in the environment and whether each of the persons in the environment is wearing the eye protection.

* * * * *